US009226708B2

(12) United States Patent
Kim

(10) Patent No.: US 9,226,708 B2
(45) Date of Patent: Jan. 5, 2016

(54) METHOD AND APPARATUS FOR CONTROLLING MEDICAL DIAGNOSTIC SYSTEM, AND METHOD OF PROVIDING SUBJECT IMAGE

(71) Applicant: Samsung Electronics Co., Ltd., Suwon-si (KR)

(72) Inventor: Young-ha Kim, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 106 days.

(21) Appl. No.: 14/168,409

(22) Filed: Jan. 30, 2014

(65) Prior Publication Data

US 2014/0350381 A1   Nov. 27, 2014

(30) Foreign Application Priority Data

May 23, 2013  (KR) ........................ 10-2013-0058548

(51) Int. Cl.
*A61B 5/00*   (2006.01)
*A61B 5/01*   (2006.01)
(Continued)

(52) U.S. Cl.
CPC ............. *A61B 5/4848* (2013.01); *A61B 5/0035* (2013.01); *A61B 5/0075* (2013.01); *A61B 5/0077* (2013.01); *A61B 5/015* (2013.01); *A61B 5/7282* (2013.01); *A61B 5/746* (2013.01); *A61B 5/7425* (2013.01); *A61B 5/7475* (2013.01); *A61B 6/032* (2013.01); *A61B 6/463* (2013.01); *A61B 6/481* (2013.01); *A61B 6/504* (2013.01);
(Continued)

(58) Field of Classification Search
CPC .. A61B 5/0035; A61B 5/0075; A61B 5/0077; A61B 5/015; A61B 5/4848; A61B 5/7282; A61B 5/7425; A61B 5/746; A61B 5/7475; A61B 6/032; A61B 6/463; A61B 6/467; A61B 6/481; A61B 6/504; A61B 6/54; A61B 6/541; A61M 5/007; A61M 5/16831; G01R 33/5601

See application file for complete search history.

(56) References Cited

U.S. PATENT DOCUMENTS 4,439,156 A   3/1984  Marshall et al.
5,305,100 A   4/1994  Choi
(Continued)

FOREIGN PATENT DOCUMENTS

JP   2008-253468 A   10/2008
JP   2012-20174 A    2/2012

OTHER PUBLICATIONS

Communication issued by the Korean Intellectual Property Office, Dated Jun. 23, 2014, In counterpart Korean Application No. 10-2013-0058548.

(Continued)

*Primary Examiner* — Michael Rozanski
(74) *Attorney, Agent, or Firm* — Sughrue Mion, PLLC

(57) ABSTRACT

A method of controlling a medical diagnostic system using a contrast medium is provided. The method includes injecting the contrast medium into a subject; obtaining an appearance image of the subject via a first camera; obtaining a temperature distribution image of the subject via a second camera; displaying a fusion image which combines the appearance image of the subject and the temperature distribution image of the subject on a screen; determining whether a side effect of the contrast medium has occurred in the subject, based on the fusion image; and selectively controlling the medical diagnostic system depending on a result of the determining.

45 Claims, 23 Drawing Sheets

(51) Int. Cl.
 *G01R 33/48* (2006.01)
 *A61B 6/03* (2006.01)
 *A61B 6/00* (2006.01)
 *G01R 33/56* (2006.01)
 *A61M 5/00* (2006.01)
 *A61M 5/168* (2006.01)

(52) U.S. Cl.
 CPC ............ *A61B 6/54* (2013.01); *A61M 5/007* (2013.01); *A61M 5/16831* (2013.01); *A61B 6/467* (2013.01); *A61B 6/541* (2013.01); *G01R 33/5601* (2013.01)

(56) References Cited

U.S. PATENT DOCUMENTS 5,842,978 A    12/1998  Levy
7,397,380 B1    7/2008  Smolsky
2011/0001809 A1*  1/2011  McManus et al. ............. 348/61

OTHER PUBLICATIONS

Notice of Allowance Issued by the Korean Intellectual Property Office, Dated Dec. 15, 2014, In counterpart Korean Application No. 10-2013-0058548.

* cited by examiner

FIG. 15
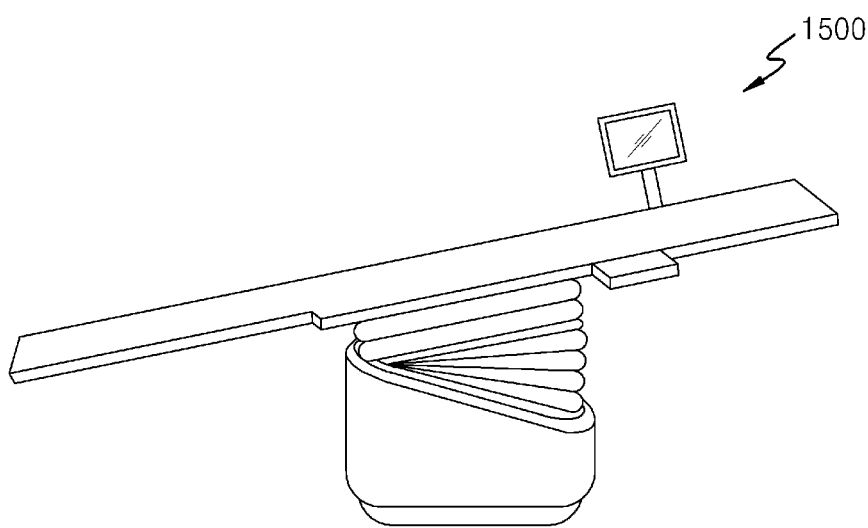
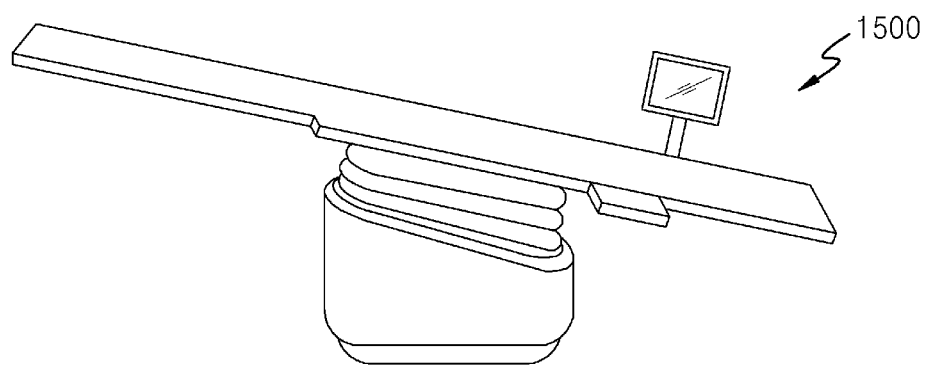

METHOD AND APPARATUS FOR CONTROLLING MEDICAL DIAGNOSTIC SYSTEM, AND METHOD OF PROVIDING SUBJECT IMAGE

CROSS-REFERENCE TO RELATED PATENT APPLICATION

This application claims the benefit of Korean Patent Application No. 10-2013-0058548, filed on May 23, 2013, in the Korean Intellectual Property Office, the disclosure of which is incorporated herein in its entirety by reference.

BACKGROUND

1. Field

Exemplary embodiments relate to a method and an apparatus for controlling a medical diagnostic system in which it may be determined whether or not a side effect of the contrast medium has occurred in a subject based on changes in an appearance image and a temperature distribution image of the subject to rapidly respond to the occurrence of a side effect of the contrast medium, and a method of providing a subject's image.

2. Description of the Related Art

In a medical test using an injection of a contrast medium, typically 100 cc or more of an iodine injection solution is injected into the body of a subject in order to capture a medical image. Although having been approved by the U.S Food and Drug Administration (FDA) in terms of safety, side reactions due to the contrast medium are frequent depending on a physical constitution of the subject. In computerized tomography (CT) scanning using a large amount of a contrast medium, side reactions due to the contrast medium occur in the subject more often than in magnetic resonance imaging (MRI) which uses a smaller amount of the contrast medium.

To rapidly determine whether a side effect of the contrast medium has occurred, a radiotherapist may check an electrocardiogram (ECG) during a heart test. However, in imaging an abdomen or a brain region, determining whether or not a side effect of the contrast medium has occurred in the subject may be based only on monitoring by a radiotherapist without checking an ECG. The radiotherapist may monitor a facial expression of the subject, but this type of subjective monitoring may be inaccurate in determining whether or not a side effect of the contrast medium has occurred in the subject. It is also impossible for the radiotherapist to rapidly respond to an occurrence of a side effect of the contrast medium in the subject.

SUMMARY

The exemplary embodiments provide a method and apparatus for automatically controlling a medical diagnostic system via a determination as to whether or not a side effect of a contrast medium has occurred in a subject based on a fusion image of an appearance image and a temperature distribution image of the subject.

The exemplary embodiments also provide a method of providing an appearance image of a subject, a temperature distribution image of the subject, or a fusion image of the appearance image and the temperature distribution image of the subject.

According to an aspect of an exemplary embodiment, there is provided a method of controlling a medical diagnostic system using a contrast medium, the method including: injecting the contrast medium into a subject; obtaining an appearance image of the subject via a first camera; obtaining a temperature distribution image of the subject via a second camera; displaying a fusion image which combines the appearance image of the subject and the temperature distribution image of the subject on a screen; determining whether a side effect of the contrast medium has occurred in the subject, based on the fusion image; and selectively controlling the medical diagnostic system depending on a result of the determining.

According to an exemplary embodiment, the first camera may be a closed-circuit television (CCTV) camera, and the second camera may be an infrared camera.

According to an exemplary embodiment, the displaying of the fusion image may include: displaying a set-up window configured to input respective transparency levels of the appearance image of the subject and the temperature distribution image of the subject on the screen; receiving an input of the respective transparency levels via the set-up window; and displaying the fusion image based on the input of the respective transparency levels.

According to an exemplary embodiment, the displaying of the fusion image may include: updating the fusion image in real-time; and displaying the updated fusion image on the screen.

According to an exemplary embodiment, the determining of whether the side effect of the contrast medium has occurred in the subject may include: analyzing a facial expression change of the subject based on the appearance image of the subject; and determining whether the side effect of the contrast medium has occurred in the subject, based on the analyzed facial expression change of the subject.

According to an exemplary embodiment, the determining of whether the side effect of the contrast medium has occurred in the subject may include: analyzing a temperature change of the subject based on the temperature distribution image; and determining whether the side effect of the contrast medium has occurred in the subject, based on the analyzed temperature change of the subject.

According to an exemplary embodiment, the analyzing of the temperature change of the subject may include: defining an interest region in the appearance image of the subject; and analyzing a temperature change of the subject in the interest region.

According to an exemplary embodiment, the defining of the interest region in the appearance image of the subject may include defining a plurality of interest regions based on user input.

According to an exemplary embodiment, the determining of whether the side effect of the contrast medium has occurred in the subject, based on the analyzed temperature change of the subject, may include: comparing a predefined reference temperature with a temperature of the subject in the interest region; and determining whether the side effect of the contrast medium has occurred in the subject, based on a result of the comparing.

According to an exemplary embodiment, the comparing may include comparing a predefined reference temperature variation with a temperature variation of the subject in the interest region.

According to an exemplary embodiment, the comparing may include comparing a predefined reference average temperature with an average temperature of the subject in the interest region.

According to an exemplary embodiment, the selectively controlling of the medical diagnostic system may include outputting an alarm signal when the temperature of the subject in the interest region is higher than the predefined reference temperature.

According to an exemplary embodiment, the selectively controlling of the medical diagnostic system may include controlling a contrast medium injection device for injecting the contrast medium into the subject.

According to an exemplary embodiment, the selectively controlling of the contrast medium injection device may include controlling the contrast medium injection device to block the injection of the contrast medium when it is determined that the side effect of the contrast medium has occurred in the subject.

According to an exemplary embodiment, the selectively controlling of the medical diagnostic system may include controlling a medical image acquisition device to discontinue capturing of a medical image of the subject.

According to an exemplary embodiment, the selectively controlling of the medical diagnostic system may include displaying at least one of a button for blocking the injecting of the contrast medium and a button for discontinuing capturing of a medical image of the subject on the screen when it is determined that the side effect of the contrast medium has occurred in the subject.

According to an exemplary embodiment, the selectively controlling of the medical diagnostic system may include: displaying a button for blocking the injecting of the contrast medium and simultaneously discontinuing capturing of a medical image of the subject on the screen when it is determined that the side effect of the contrast medium has occurred in the subject; and transmitting a control command for blocking the injecting of the contrast medium to the contrast medium injection device, and transmitting a control command for discontinuing the capturing of a medical image of the subject to a medical image acquisition device, in response to a user's selection of the button being input.

According to an exemplary embodiment, the selectively controlling of the medical diagnostic system may include requesting a preselected external device to initiate a voice connection or transmitting a notification message, when it is determined that the side effect of the contrast medium has occurred in the subject.

According to another aspect of an exemplary embodiment, there is provided a method of controlling a medical diagnostic system using a contrast medium, the method including: injecting the contrast medium into a subject; obtaining an appearance image of the subject via a first camera; obtaining a temperature distribution image of the subject, via a second camera; displaying the appearance image and the temperature distribution image of the subject on a screen; determining whether a side effect of the contrast medium has occurred in the subject, based on at least one of the appearance image of the subject and the temperature distribution image of the subject; and selectively controlling the medical diagnostic system depending on a result of the determining.

According to another aspect of an exemplary embodiment, there is provided a method of providing an image of a subject, the method including: injecting a contrast medium into the subject; obtaining an appearance image of the subject via a first camera; obtaining a temperature distribution image of the subject via a second camera; creating a fusion image which combines the appearance image and the temperature distribution image of the subject; and displaying the fusion image on a screen.

According to another aspect of an exemplary embodiment, there is provided a method of controlling a medical diagnostic system using a contrast medium, the method including: injecting the contrast medium into a subject; displaying a temperature distribution image of the subject; determining whether a side effect of the contrast medium has occurred in the subject, based on the temperature distribution image; and selectively controlling the medical diagnostic system depending on a result of the determining.

According to another aspect of an exemplary embodiment, there is provided a method of controlling a medical diagnostic system using a contrast medium, the method including: injecting the contrast medium into a subject; displaying an appearance image of the subject; analyzing a facial expression change of the subject based on the appearance image of the subject; determining whether a side effect of the contrast medium has occurred in the subject, based on the analyzed facial expression change of the subject; and selectively controlling the medical diagnostic system depending on a result of the determining.

According to another aspect of an exemplary embodiment, there is provided an apparatus configured to control a medical diagnostic system, the apparatus including: a first camera configured to obtain an appearance image of the subject into whom a contrast medium has been injected; a second camera configured to obtain a temperature distribution image of the subject; a display unit configured to display a fusion image which combines the appearance image of the subject and the temperature distribution image of the subject on a screen; and a control unit configured to make a determination as to whether a side effect of the contrast medium has occurred in the subject, based on the fusion image, and to selectively control the medical diagnostic system depending on a result of the determination.

According to an exemplary embodiment, the medical diagnostic system may include at least one of a medical image acquisition device configured to obtain a medical image of the subject and a contrast medium injection device configured to automatically inject the contrast medium into the subject.

According to an exemplary embodiment, the medical image acquisition device may include at least one of a computed tomography (CT) image scanning apparatus, an angiography apparatus, and a magnetic resonance imaging (MRI) apparatus.

According to an exemplary embodiment, the display unit may be configured to display a set-up window for inputting respective transparency levels of the appearance image of the subject and the temperature distribution image of the subject.

According to an exemplary embodiment, the apparatus configured to control a medical diagnostic system may further include a user input unit configured to receive an input of the respective transparency levels via the set-up window, wherein the display unit is configured to display the fusion image based on the input of the respective transparency levels.

According to an exemplary embodiment, the control unit may be configured to analyze a facial expression change of the subject based on the appearance image of the subject, and determine whether or not the side effect of the contrast medium has occurred in the subject, based on the analyzed facial expression change of the subject.

According to an exemplary embodiment, the control unit may be configured to analyze a temperature change of the subject based on the temperature distribution image and determine whether the side effect of the contrast medium has occurred in the subject, based on the analyzed temperature change of the subject.

According to an exemplary embodiment, the control unit may be configured to define an interest region in the appearance image of the subject and analyze a temperature change of the subject in the interest region.

According to an exemplary embodiment, the apparatus configured to control a medical diagnostic system may further include a user input unit configured to receive a user input defining a plurality of interest regions.

According to an exemplary embodiment, the control unit may be configured to compare a predefined reference temperature and a temperature of the subject in the interest region, and determine whether the side effect of the contrast medium has occurred in the subject, based on a result of the comparison.

According to an exemplary embodiment, the predefined reference temperature may include at least one of a predefined reference absolute temperature, a predefined reference average temperature and a predefined reference temperature variation.

According to an exemplary embodiment, the control unit may be configured to output an alarm signal when the temperature of the subject in the interest region is higher than the predefined reference temperature.

According to an exemplary embodiment, the control unit may be configured to control a contrast medium injection device to block the injection of the contrast medium when it is determined that the side effect of the contrast medium has occurred in the subject.

According to an exemplary embodiment, the control unit may be configured to control a medical image acquisition device to discontinue capturing of a medical image of the subject when it is determined that the side effect of the contrast medium has occurred in the subject.

According to an exemplary embodiment, the display unit may be configured to display at least one of a button which blocks the injection of the contrast medium and a button which discontinues capturing of a medical image of the subject when it is determined that the side effect of the contrast medium has occurred in the subject.

According to an exemplary embodiment, the display unit may be configured to display a button which blocks the injection of the contrast medium and simultaneously discontinues capturing of a medical image of the subject when it is determined that the side effect of the contrast medium has occurred in the subject, and the control unit may be configured to transmit a control command which blocks the injection of the contrast medium to a contrast medium injection device, and transmit a control command which discontinues capturing of a medical image of the subject to a medical image acquisition device, when a user's selection of the button is received.

According to an exemplary embodiment, the control unit may be configured to request a preselected external device to initiate a voice connection or transmit a notification message, when it is determined that the side effect of the contrast medium has occurred in the subject.

According to another aspect of an exemplary embodiment, there is provided an apparatus configured to control a medical diagnostic system, the apparatus including: a first camera configured to obtain an appearance image of a subject into whom a contrast medium is injected; a second camera configured to obtain a temperature distribution image of the subject; a display unit configured to display the appearance image of the subject and the temperature distribution image of the subject; and a control unit configured to make a determination as to whether a side effect of the contrast medium has occurred in the subject, based on at least one of the appearance image of the subject and the temperature distribution image of the subject, and to selectively control the medical diagnostic system depending a result of the determination.

According to another aspect of an exemplary embodiment, there is provided an apparatus configured to control a medical diagnostic system, the apparatus including: a first camera configured to obtain an appearance image of a subject into whom a contrast medium has been injected; a second camera configured to obtain a temperature distribution image of the subject; an image processing unit configured to create a fusion image which combines the appearance image of the subject and the temperature distribution image of the subject; a display unit configured to display the fusion image; and a control unit configured to control the first camera, the second camera, the image processing unit, and the display unit.

BRIEF DESCRIPTION OF THE DRAWINGS

The above and other features and advantages of the exemplary embodiments will become more apparent by describing in detail exemplary embodiments thereof with reference to the attached drawings in which:

FIG. 15 is a diagram for describing adjusting an angle of a table of a medical image acquisition device, according to an exemplary embodiment;

DETAILED DESCRIPTION OF THE EXEMPLARY EMBODIMENTS

As used herein, the term "and/or" includes any and all combinations of one or more of the associated listed items. Expressions such as "at least one of," when preceding a list of elements, modify the entire list of elements and do not modify the individual elements of the list.

General and widely-used terms have been employed herein, in consideration of functions provided in the present disclosure, and may vary according to an intention of one of ordinary skill in the art, a precedent, or emergence of new technologies. Additionally, in some cases, an applicant may arbitrarily select specific terms. Then, the applicant will provide the meaning of the terms in the description of the present disclosure. Accordingly, it will be understood that the terms used herein should be interpreted as having a meaning that is consistent with their meaning in the context of the relevant art and will not be interpreted in an idealized or overly formal sense unless expressly so defined herein.

It will be further understood that the terms "comprises", "comprising", "includes", and/or "including" when used herein, specify the presence of components, but do not preclude the presence or addition of one or more other components, unless otherwise specified. Additionally, terms used herein, such as 'unit' or 'module', refer to entities for processing at least one function or operation. These entities may be implemented by hardware, software, or a combination of hardware and software.

As used herein, the term "image" may refer to multi-dimensional data consisting of discrete image elements (for example, pixels of a 2-dimensional image and voxels of a 3-dimensional image).

The present disclosure will now be described more fully with reference to the accompanying drawings, in which exemplary embodiments are shown. The exemplary embodiments may, however, be embodied in many different forms and should not be construed as being limited to the exemplary embodiments set forth herein. In the description of the present disclosure, certain detailed explanations of the related art are omitted when it is deemed that the detailed explanation may unnecessarily obscure the essence of the exemplary embodiments Like numbers refer to like elements throughout the description of the figures.

Figure 1:
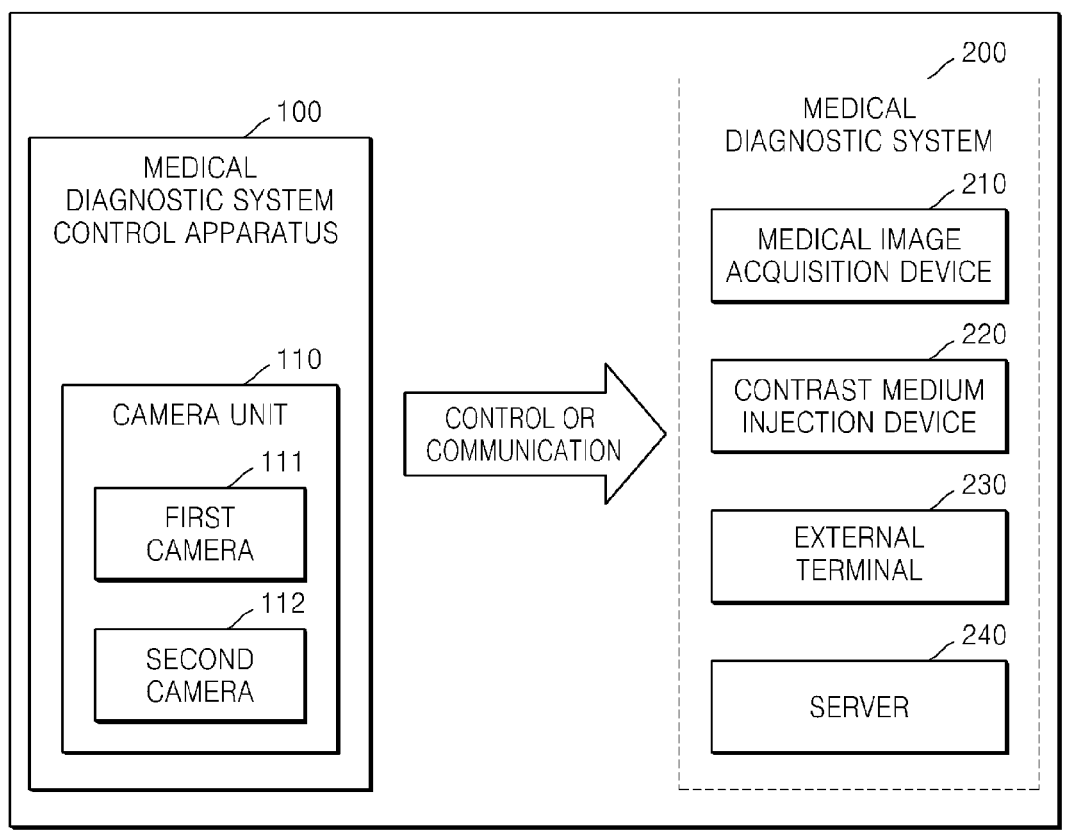
FIG. 1 is a block diagram of a medical system according to an exemplary embodiment.

FIG. 1 is a block diagram of a medical system according to an exemplary embodiment.

Referring to FIG. 1, the medical system may include a medical diagnostic system control apparatus (hereinafter, a 'control apparatus') 100 and a medical diagnostic system 200.

According to an exemplary embodiment, the control apparatus 100 may determine whether or not a side effect of a contrast medium has occurred in a subject, and control the medical diagnostic system 200 based on a result of the determination. According to an exemplary embodiment, the control apparatus 100 may include a display apparatus for providing at least one of an appearance image of the subject, a temperature distribution image of the subject, and a fusion image fusing together the appearance image and the temperature distribution image of the subject.

According to an exemplary embodiment, the control apparatus 100 includes a camera unit 110 for capturing a subject. For example, the control apparatus 100 may include at least one of a first camera 111 for obtaining an appearance image of the subject and a second camera 112 for obtaining a temperature distribution image of the subject. The camera unit 110 for capturing a subject will be described later in greater detail with reference to FIG. 3.

The control apparatus 100 may be implanted in various forms. For example, the control apparatus 100 as used herein may be implemented as a fixed terminal or a mobile terminal. Non-limiting examples of the mobile terminal include a smartphone, a laptop computer, a personal data assistant (PDA), and a tablet PC.

In some other exemplary embodiments, the control apparatus 100 may be implemented as hardware or software of a medical image acquisition device 210 or as an apparatus separate from the medical image acquisition device 210.

According to an exemplary embodiment, the control apparatus 100 may communicate with the medical diagnostic system 200 in a wired or wireless mode. For example, the control apparatus 100 may control the medical diagnostic system 200 via any of various communication methods. According to an exemplary embodiment, the control apparatus 100 may communicate with an external terminal 230 via a text message session, a voice call session, or a video call session.

According to an exemplary embodiment, the control apparatus 100 may transmit data to or receive the same from a hospital server or another medical apparatus in a hospital that is connected to the control apparatus 100 via a picture archiving and communication system (PACS). The control apparatus 100 may perform data communication with a server 240 in compliance with the Digital Imaging and Communications in Medicine (DICOM) standard.

According to an exemplary embodiment, the control apparatus 100 may include a touch screen. The touch screen may be configured to detect a touch input position, a touch input area, and a touch input pressure. For example, the tough screen may be configured to detect a direct real touch and a proximity touch.

As used herein, a "real-touch" refers to touching a screen with a touch tool (for example, a finger or an electronic stylus), and a "proximity-touch" refers to approaching, not touching, a screen with a touch tool while maintaining a predetermined distance between the screen and the touch tool.

According to an exemplary embodiment, the control apparatus 100 may sense a user's touch gesture on an ultrasonic image via a touch screen. As used herein, touch gestures (touch inputs) of a user may be, for example, a tap, a touch and hold, a double-tap, a drag, panning, a flick, a drag-and-drop, a swipe, and a pinch.

A "tap" is a gesture in which a user touches a screen by using a finger or a touch tool, for example, an electronic pen, and then immediately lifts the finger or touch tool off the screen without dragging on the screen.

A "touch and hold" is a gesture in which a user touches a screen by using a finger or a touch tool, for example, an electronic pen, and holds the touch for more than a critical period of time, for example, 2 seconds. That is, a difference in time between time points of a touch on and a lift-off from the screen is longer than the critical period of time, for example, 2 seconds. If the touch input is held for more than the critical period of time, a feedback signal may be visually, aurally, or tactually provided to enable a user to recognize that the touch input is a touch and hold. The critical period of time may vary according to exemplary embodiments.

A "double tap" is a gesture in which a user touches a screen twice by using a finger or a touch tool which may be a stylus.

A "drag" is a gesture in which a user touches a screen by using a finger or a touch tool and moves the finger or the touch tool to another location in the screen while holding the touch. When the drag is performed, an object moves, or a panning gesture, which is described below, is performed.

A "panning" gesture is a gesture in which a user performs a drag without selecting an object. As the panning does not select a specific object, an object does not move in a page, and the page moves in the screen or a group of objects moves in the page.

A "flick" is a gesture in which a user performs a drag at a critical speed or at a higher speed, for example, 100 pixels per second, by using a finger or a touch tool. The flick may be distinguished from the drag or the panning based on whether a moving speed of a finger or a touch tool is equal to or higher than the critical speed, for example, 100 pixels/s.

A "drag and drop" is a gesture in which a user drags an object to a predetermined place in a screen by using a finger or a touch tool, and then, lifts the finger or touch tool off the screen.

A "pinch" is a gesture in which a user touches a screen with two fingers and moves the two fingers in different directions. The pinch may be a pinch-open gesture for zooming-in to an object or a page, or a pinch-close gesture for zooming-out from an object or a page. A zoom-in or zoom-out value is determined according to a distance between the two fingers.

A "swipe" is a gesture for touching an object in a screen by using a finger or a touch tool and moving the finger or the touch tool in a horizontal or vertical direction for a certain distance. Moving in a diagonal direction may not be recognized as a swipe event.

According to an exemplary embodiment, the control apparatus 100 may provide some or all of the buttons for controlling the medical diagnostic system 200 via a graphical user interface (GUI)-based touch screen.

The medical diagnostic system 200 may include a medical image acquisition device 210, a contrast medium injection device 220, an external terminal 230, and a server 240, but is not limited thereto. That is, these listed elements of the medical diagnostic system 200 are not essential elements. For example, the medical diagnostic system 200 may be implemented to include more or less elements than the elements illustrated in FIG. 1.

According to an exemplary embodiment, the medical image acquisition device 210 may obtain a medical image by using a contrast medium. Non-limiting examples of the medical image acquisition device 210 include a computerized tomography (CT) image scanning apparatus, a magnetic resonance imaging (MRI) apparatus, and an angiography apparatus.

A CT image scanning apparatus which provides a cross-sectional image of an object may express an internal structure of an object (for example, an organ, such as kidneys, lungs or the like) such that the internal structure does not overlap compared to an X-ray imaging apparatus. For example, the CT image scanning apparatus may capture and process tens or hundreds of images per second, have a thickness of about 2 mm or less, and provide a relatively accurate cross-sectional image of the object.

An MRI apparatus may express a magnitude of a magnetic resonance (MR) signal corresponding to a radio frequency (RF) signal generated at a magnetic field intensity as a contrast, thereby obtaining a cross-sectional image of an object. For example, when an instantaneous radiation of an RF signal onto a subject laying in a strong magnetic field is interrupted, an MR signal may be emitted from a specific atomic nucleus (for example, a proton nucleus) that resonates as a result. The MRI apparatus may receive the MR signal to obtain an MR image therefrom. An MR signal refers to an RF signal reflected off of an object in response to irradiation of an RF signal onto the object. The magnitude of an MR signal may be dependent on a concentration of atoms (for example, hydrogen atoms) in the object, a T1 relaxation time, a T2 relaxation time, or a blood flow in the object.

An angiography apparatus uses X-ray radiation to visualize a blood vessel (an artery or vein) of the subject into whom a contrast medium has been injected via a catheter having a diameter of about 2 mm or so.

The contrast medium injection device 220 may refer to a device for injecting a contrast medium into a blood vessel or tissue of a subject. A contrast medium refers to a chemical injected into a tissue or vessel of a subject to artificially increase a difference in X-ray absorption between tissues or vessels. The injection of the contrast medium increases a difference in X-ray absorption, and consequentially enhances a contrast of a medical image, which enables a user to focus on observing a site of interest.

The external terminal 230 may be a device connected to the control apparatus 100 for communication. Non-limiting examples of the external terminal 230 include a doctor's terminal, a nurse's terminal, or a radiotherapist's terminal. The external terminal may transmit data or receive data for short-range communication with the control apparatus 100. In this regard, available short-range wireless communication technologies include, but are not limited to, radio local area network (Wi-Fi), Bluetooth, ZigBee, Wi-Fi Direct (WFD), Ultra Wideband (UWB), Infrared Data Association (IrDA), Bluetooth Low Energy (BLE), Near Field Communication (NFC), and the like.

In exemplary embodiments, Wi-Fi may be implemented in an infrastructure mode in which a plurality of terminals having access points (APs) for wireless transmission within a predetermined radius transmit or receive data to or from each other, and an ad hoc mode in which a plurality of terminals transmit or receive data to or from each other in a peer-to-peer (P2P) form without an AP.

Bluetooth is a wireless technology standard for communications at a low power level between wireless communication devices over short distances. UWB is a radio technology for transmission of a large quantity of digital data at a low power level over a wide range of spectrum frequencies.

WFD is a new version of Wi-Fi technologies that enables devices equipped with WFD to directly communicate with each other, i.e., without a hotspot, a router, or an AP, to share information. ZigBee, which is an IEEE 802.15.4 standard supporting short-range communication, is a wireless network technology for short-range communication within about 10 m to 20 m at home or offices and for ubiquitous computing.

BLE is a short-range communication technology and functions as the core technology of Bluetooth 4.0. Compared to the classic Bluetooth standard, BLE provides a relatively short duty cycle, lower production cost, and reduced power consumption in terms of average power and standby power so that devices operate for several years even with a coin-sized battery.

NFC is a communication technology using a contactless near field radio communication unit as a radio-frequency identification (RFID) tag using a frequency of 13.56 MHz, which enables data transmission between neighboring terminals at a distance of 10 cm. NFC may include a P2P mode, a reader/writer (R/W) mode, and a card emulation mode.

The server 240 may receive information about a status of the subject from the control apparatus 100. For example, the server 240 may receive information about whether or not a side effect of the contrast medium has occurred in the subject from the control apparatus 100.

According to an exemplary embodiment, the server 240 may be a hospital server connected via a picture archiving and communication system (PACS), or another server connected to the hospital server.

Hereinafter, a method by which the control apparatus 100 controls the medical diagnostic system 200 based on whether a side effect of the contrast medium has occurred in the subject, according to an exemplary embodiment, will be described in greater detail with reference to FIG. 2.

Figure 2:
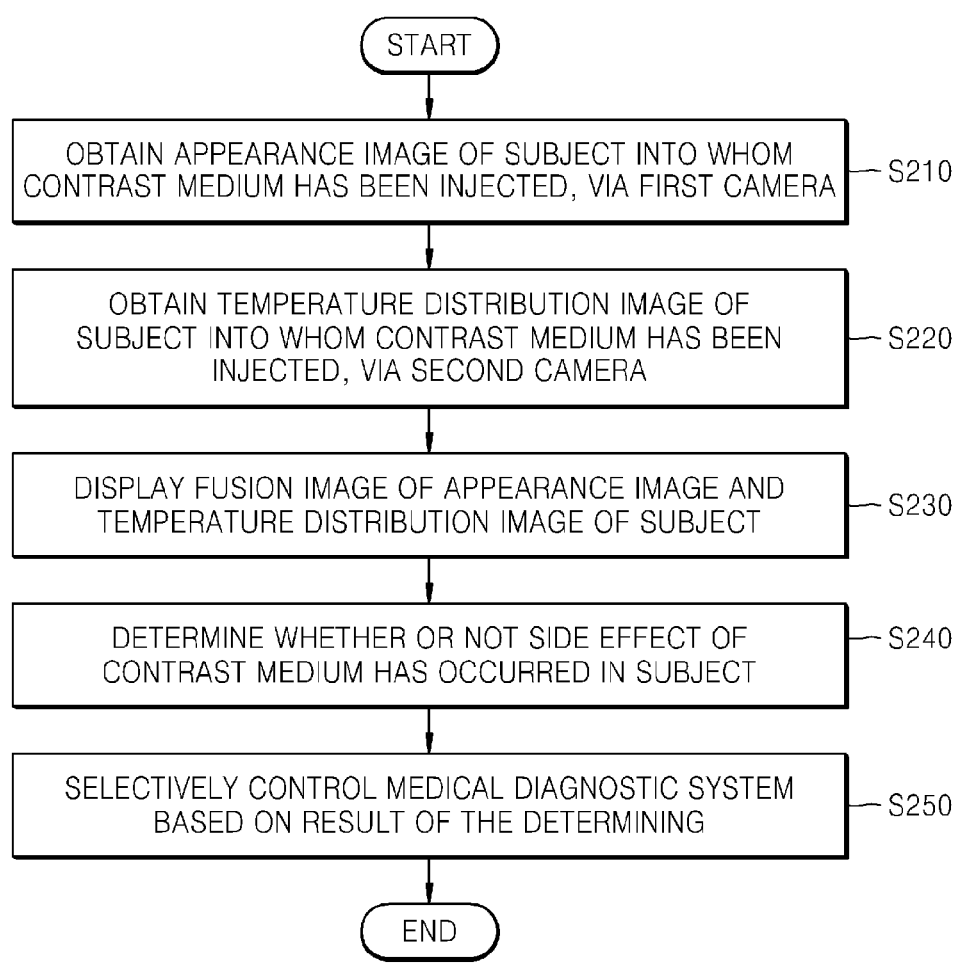
FIG. 2 is a flowchart of a method of controlling a medical diagnostic system, according to an exemplary embodiment.

FIG. 2 is a flowchart of a method of controlling a medical diagnostic system, according to an exemplary embodiment.

In operation S210, the control apparatus 100 obtains an appearance image of a subject into whom a contrast medium has been injected, via the first camera 111. Non-limiting examples of the first camera 111 include a closed-circuit television (CCTV) camera and a webcam. For example, the first camera 111 may be any camera able to capture an appearance image of a subject.

A CCTV camera refers to a camera for transmitting an image signal of a selected area to a monitor (for example, the control apparatus 100). A webcam, which is a compound word of web and camera, refers to a camera used for broadcasting content onto the Internet. Hereinafter, for convenience of explanation, exemplary embodiments will be described with reference to a CCTV camera as the first camera 111.

According to an exemplary embodiment, the appearance image of the subject may include information about a facial expression change of the subject. According to an exemplary embodiment, the appearance image of the subject may be a 2-dimensional or a 3-dimensional image. According to an exemplary embodiment, the appearance image of the subject may be a real-time image obtained beginning from the injection of the contrast medium into a blood vessel or tissue of the subject. For example, the appearance image of the subject may be a real-time image varying in real time with a facial expression change of the subject.

In operation S220, the control apparatus 100 may obtain a temperature distribution image of the subject into whom the contrast medium has been injected, via the second camera 112. A non-limiting example of the second camera 112 is an infrared camera. An infrared camera may detect infrared radiant energy radiated from an object and transform the radiation temperature of the object into an electrical signal to display a 2-dimensional visible image.

According to an exemplary embodiment, the temperature distribution image of the subject refers to an image obtained via visualization of the body temperature of the subject. According to an exemplary embodiment, the control apparatus 100 may express the temperature distribution image of the subject in various forms by mapping the body temperature of the subject to colors, contrasts, patterns, or contours. According to an exemplary embodiment, the temperature distribution image of the subject may be a real-time image obtained beginning from the injection of the contrast medium into a blood vessel or tissue of the subject. For example, the temperature distribution image of the subject may be a real-time image varying in real time with a temperature change of the subject.

According to an exemplary embodiment, the first camera 111 and the second camera 112 may be implemented as one integrated camera or separate cameras.

In operation S230, the control apparatus 100 may display a fusion image of the appearance image and the temperature distribution image of the subject on a screen.

According to an exemplary embodiment, the control apparatus 100 may create and display a fusion image on the screen, or may display an externally received fusion image on the screen. According to an exemplary embodiment, the control apparatus 100 may create a fusion image by combining the appearance image and the temperature distribution image. According to another exemplary embodiment, the control apparatus 100 may externally transmit the appearance image and the temperature distribution image of the subject and receive an externally created fusion image thereof. Hereinafter, for convenience of explanation, exemplary embodiments will be described with reference to a case where the control apparatus 100 creates a fusion image.

According to an exemplary embodiment, the control apparatus 100 may control a fusion ratio or respective transparency levels of the appearance image and the temperature distribution image of the subject based on user input, for example, a radiotherapist's input.

For example, the control apparatus 100 may display a set-up window for inputting respective transparency levels of the appearance image and the temperature distribution image of the subject on the screen. The control apparatus 100 may receive an input of the respective transparency levels of the appearance image and the temperature distribution image of the subject via the set-up window. In this regard, the control apparatus 100 may display a fusion image of the appearance image and the temperature distribution image of the subject based on the input of the respective transparency levels. For example, when the appearance image of the subject has a transparency level of 100%, only the temperature distribution image may appear in the fusion image. On the other hand, when the temperature distribution image of the subject has a transparency level of about 100%, only the appearance image of the subject may appear in the fusion image. That is, the higher the transparency level of an image, the lower the percentage of the image in the fusion image may be displayed. This will be described later in greater detail with reference to FIGS. 5 and 6.

According to an exemplary embodiment, the control apparatus 100 may update the fusion image in real-time. The control apparatus 100 may update the fusion image at a predefined interval. The predefined interval of update may be set by the control apparatus 100 or by a user, for example, a radiotherapist. According to an exemplary embodiment, the control apparatus 100 may display an updated fusion image in real time on the screen.

In operation S240, the control apparatus 100 may determine whether or not a side effect of the contrast medium has occurred in the subject, based on the fusion image.

According to an exemplary embodiment, the control apparatus 100 may analyze a facial expression change of the subject based on the appearance image of the subject in the fusion image. The control apparatus 100 may determine whether or not a side effect of the contrast medium has occurred in the subject based on the facial expression change of the subject. For example, the control apparatus 100 may measure a facial expression change rate of the subject and compare the measured facial expression change rate of the subject with a predefined reference facial expression change rate (for example, 20%). When the measured facial expression change rate of the subject is greater than a predefined reference facial expression change rate of, for example, 20%, the control apparatus 100 may determine that a side effect of the contrast medium has occurred in the subject.

According to another exemplary embodiment, the control apparatus 100 may determine a temperature change of the subject based on the temperature distribution image of the subject in the fusion image. The control apparatus 100 may determine whether a side effect of the contrast medium has occurred in the subject based on the temperature change of the subject.

For example, the control apparatus 100 may determine whether or not a side effect of the contrast medium has occurred in the subject based on a result of comparing an amount of temperature change of the subject with a predefined amount of temperature change of, for example, about 3° C. According to an exemplary embodiment, the control apparatus 100 may determine whether or not a side effect of the contrast medium has occurred in the subject based on a result of comparing a temperature change of the subject with a predefined reference temperature of, for example, 39° C.

According to an exemplary embodiment, the control apparatus 100 may determine whether or not a side effect of the contrast medium has occurred in the subject, based on a temperature change in an interest region. The interest region may be automatically defined by the control apparatus 100 or manually by a user, for example, a radiotherapist. According to exemplary embodiment, one interest region or at least two interest regions may be defined.

According to an exemplary embodiment, the control apparatus 100 may define an interest region in the appearance image of the subject. According to another exemplary embodiment, the control apparatus 100 may define an interest region in the fusion image. For example, the control apparatus 100 may define a region around the mouth, noise, or carotid artery of the subject as an interest region.

According to an exemplary embodiment, the control apparatus 100 may compare a predefined reference temperature with the temperature of the subject in the interest region. The control apparatus 100 may determine whether or not a side effect of the contrast medium has occurred in the subject based on a result of the comparison.

For example, when a highest temperature (for example, 39.5° C.) of the subject is higher than a predefined reference temperature of, for example, 39° C., the control apparatus 100 may determine that a side effect of the contrast medium has occurred in the subject. When an amount of temperature change of the subject in the interest region (for example, 2.5° C.) is greater than a predefined reference temperature variation of, for example, 2° C., the control apparatus 100 may determine that a side effect of the contrast medium has occurred in the subject. When an average temperature of the subject in the interest region (for example, 39.3° C.) is greater than a predefined average temperature of, for example, 39° C., the control apparatus 100 may determine that a side effect of the contrast medium has occurred in the subject.

According to an exemplary embodiment, the control apparatus 100 may analyze a facial expression change and a temperature change of the subject based on the fusion image. The control apparatus 100 may determine whether or not a side effect of the contrast medium has occurred in the subject based on both information about the facial expression change of the subject and information about the temperature change of the subject For example, when a facial expression change rate of the subject is greater than a predefined reference facial change rate of, for example, 20%, and when an amount of temperature change of the subject is greater than a reference temperature variation of, for example, 3° C., the control apparatus 100 may determine that a side effect of the contrast medium has occurred in the subject.

According to an exemplary embodiment, when the control apparatus 100 determines whether or not a side effect of the contrast medium has occurred in the subject in consideration of both the facial expression change and the temperature change of the subject, accuracy of the determination may be improved.

In operation S250, the control apparatus 100 may selectively control the medical diagnostic system 200 depending on a result of the determining whether or not a side effect of the contrast medium has occurred in the subject.

According to an exemplary embodiment, the control apparatus 100 may control the contrast medium injection device 220 for injecting a contrast medium into a subject. For example, the control apparatus 100 may control the contrast medium injection device 220 to block the injection of the contrast medium when it is determined that a side effect of the contrast medium has occurred in the subject.

According to an exemplary embodiment, the control apparatus 100 may control the medical image acquisition device 210 to discontinue capturing a medical image of the subject when it is determined that a side effect of the contrast medium has occurred in the subject.

According to an exemplary embodiment, the control apparatus 100 may display at least one of a button for blocking injection of the contrast medium and a button for discontinuing capturing of a medical image of the subject on the screen when it is determined that a side effect of the contrast medium has occurred in the subject. According to another exemplary embodiment, the control apparatus 100 may display a button for blocking injection of the contrast medium and simultaneously discontinue capturing of a medical image of the subject on the screen when it is determined that a side effect of the contrast medium has occurred in the subject.

The control apparatus 100 may transmit a control command for blocking injection of the contrast medium to the contrast medium injection device 220 and transmit a control command for discontinuing capturing of a medical image of the subject of the medical image acquisition device 210, when a user's selection of the button is input.

According to an exemplary embodiment, the control apparatus 100 may generate a control command according to a control protocol of the medical image acquisition device 210 or the contrast medium injection device 220.

According to an exemplary embodiment, the control apparatus 100 may output an alarm signal when it is determined that a side effect of the contrast medium has occurred in the subject. The alarm signal may include at least one of a video signal, an audio signal, and a vibration signal. For example, when an amount of temperature change of the subject in the interest image is greater than a predefined reference temperature variation, the control apparatus 100 may output an alarm signal.

According to an exemplary embodiment, the control apparatus 100 may request a preselected external terminal 230 to initiate a voice connection or transmit a notification message to the preselected external terminal 230 when it is determined that a side effect of the contrast medium has occurred in the subject. For example, the control apparatus 100 may request a doctor's terminal or a nurse's terminal to initiate a voice connection when a side effect of the contrast medium has occurred in the subject and is considered to be an emergency.

According to an exemplary embodiment, the control apparatus 100 may control an angle of a table of the medical image acquisition device 210. For example, the control apparatus 100 may control an angle of the table of the medical image acquisition device 210 to help the subject to sit upright when it is determined that a side effect of the contrast medium has occurred in the subject.

Hereinafter, a process in which the control apparatus 100 obtains the appearance image and the temperature distribution image of the subject, according to an exemplary embodiment, will be described in greater detail with reference to FIG. 3.

Figure 3:
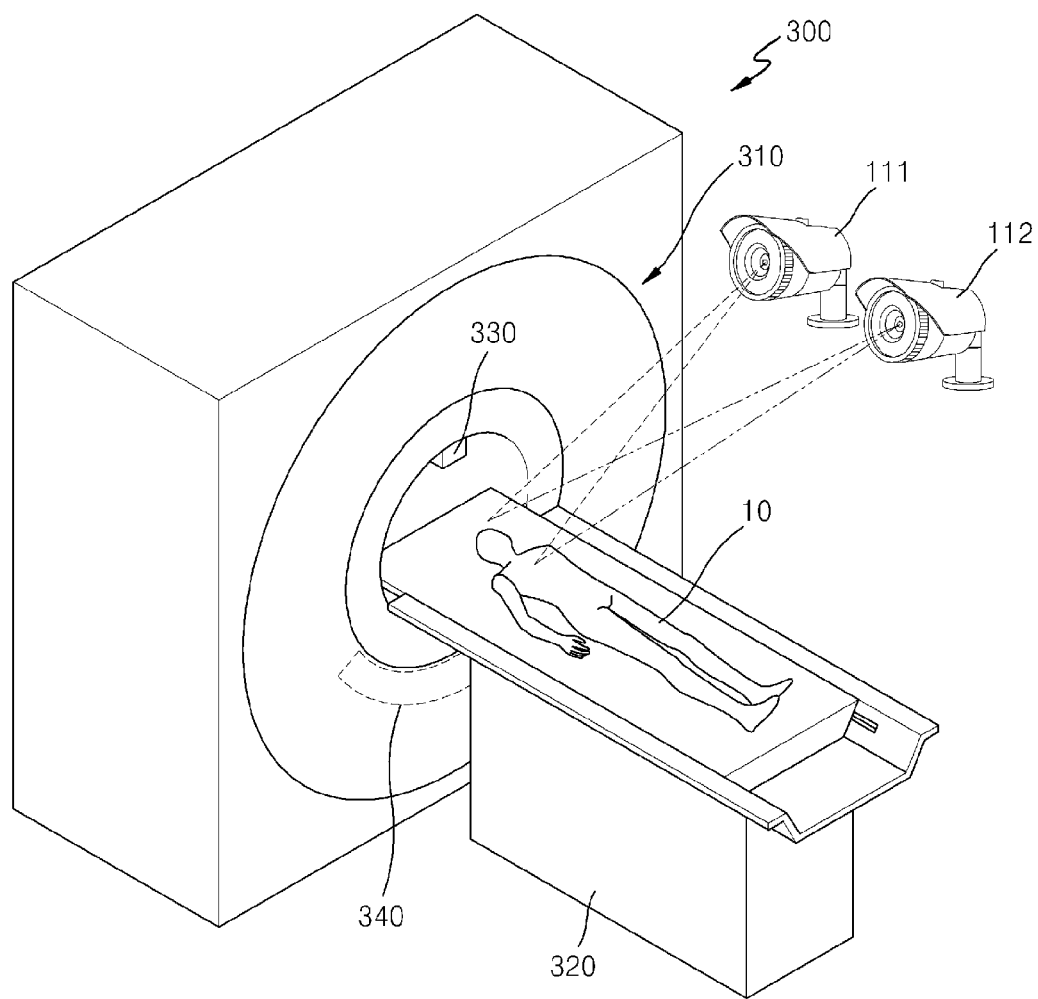
FIG. 3 is a diagram for illustrating a technique of obtaining an appearance image and a temperature distribution image of a subject, according to an exemplary embodiment.

FIG. 3 is a diagram for illustrating a technique of obtaining an appearance image and a temperature distribution image of the subject, according to an exemplary embodiment, where a CT image scanning apparatus 300 is used as an example of the medical image acquisition device 210.

Referring to FIG. 3, a subject 10 may lie down on a table 320 of the CT image scanning apparatus 300. According to an exemplary embodiment, the table 320 may be movable in one or more directions (for example, in at least one direction of upward, downward, left, and right), and the movement may be controllable by a control unit (not shown) of the CT image scanning apparatus 300.

According to an exemplary embodiment, the CT image scanning apparatus 300 may include a gantry 310. According to an exemplary embodiment, the gantry 310 may include a rotary frame (not shown), an X-ray generation unit 330, an X-ray detection unit 340, a rotary driving unit (not shown), a slip ring (not shown), a data acquisition system (DAS) (not shown), and a data transmission unit (not shown).

According to an exemplary embodiment, the gantry 310 may include an annular rotary frame rotatable about a predefined rotation axis (RA). The rotary frame may have a disc shape. The rotary frame may include the X-ray generation unit 330 and the X-ray detection unit 340 that are disposed opposite to each other to have a predefined field of view (FOV). The rotary frame may receive a driving signal from the rotary driving unit and rotate the X-ray generation unit 330 and the X-ray detection unit 340 at predefined rotation speeds.

The X-ray generation unit 330 may receive a voltage or current applied from a high-voltage generation unit, via the slip ring, to generate and emit X-rays. That is, when the high-voltage generation unit applies a predefined voltage (hereinafter, referred to as a tube voltage), the X-ray generation unit 330 may generate X-rays having a plurality of energy spectra corresponding to the predefined tube voltage. The X-rays generated by the X-ray generation unit 330 may be emitted in a predefined form, for example, as cone-shaped beams (for example, having a pyramidal shape), via a collimator (not shown).

The X-ray detection unit 340 may be positioned opposite to the X-ray generation unit 330. The X-ray detection unit 340 may include a plurality of X-ray detection devices. A single X-ray detection device may form a single channel, but is not limited thereto. The X-ray detection unit 340 may detect X-rays generated and transmitted by the X-ray generation unit 330 and passing through the subject 10, and generate an electrical signal corresponding to the intensity of the detected X-rays. The electrical signal generated from the X-ray detection unit 340 may be collected by the DAS.

According to an exemplary embodiment, a contrast medium may be injected into a blood vessel of the subject 10 in order to capture a CT image. In this regard, the control apparatus 100 may obtain an appearance image of the subject 10 via a first camera 111 and a temperature distribution image of the subject 10 via a second camera 112 to identify whether or not a side reaction of the contrast medium has occurred in the subject 10.

According to an exemplary embodiment, the first camera 111 and the second camera 112 may be a fixed camera or a mobile camera. For example, the first cameral 111 and the second camera 112 may be attached to a front, a rear, or a side of the gantry 310 to capture a predefined body part (for example, the face) of the subject 10. The first camera 111 and the second camera 112 may be attached to a ceiling rail to be movable in a predefined direction, for example, upward, downward, left, or right.

According to an exemplary embodiment, the control apparatus 100 may create a fusion image of the subject 10 from the appearance image of the subject 10 obtained via the first camera 111 and the temperature distribution image of the subject 10 obtained via the second camera 112. This will be described in greater detail with reference to FIGS. 4A, 4B, and 4C.

Figure 4:
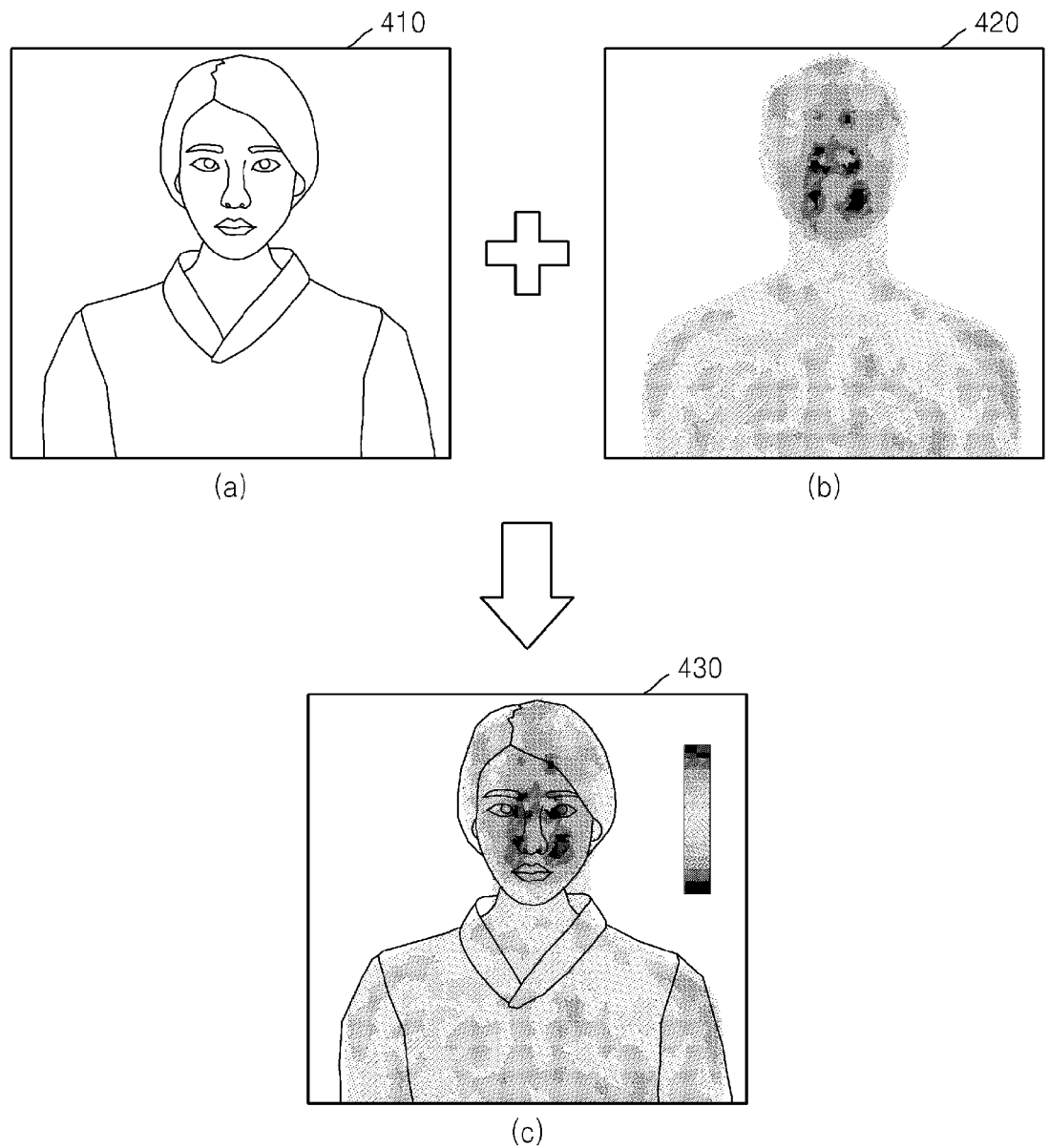
FIG. 4 shows diagrams for describing a fusion image according to an exemplary embodiment.

FIG. 4 presents diagrams for describing a fusion image according to an exemplary embodiment.

Referring to (a) of FIG. 4, the control apparatus 100 may obtain an appearance image of the subject 10 captured by the first camera 111. The control apparatus 100 may identify a facial expression change of the subject 10 from the appearance image 410 of the subject 10, which is a real appearance image of the subject 10 into whom the contrast medium has been injected.

Referring to (b) of FIG. 4, the control apparatus 100 may obtain a temperature distribution image 420 of the subject 10 captured by the second camera 112. The temperature distribution image 420 of (b) of FIG. 4 is an exemplary embodiment in which temperature distribution is represented as contrasts in the temperature distribution image 420, but other exemplary embodiments are not limited thereto. That is, the control apparatus 100 may represent the temperature distribution of the subject 10 as colors or contours, or various other ways as well.

Referring to (c) of FIG. 4, the control apparatus 100 may create a fusion image 430 of the appearance image 410 and the temperature distribution image 420 of the subject 10. The control apparatus 100 may synchronize the positions and orientations of the appearance image 410 and the temperature distribution image 420 of the subject 10 to overlap a temperature distribution of a body part region, for example, the forehead or nose of the subject 10, in the temperature distribution image 420 with a corresponding body part region (for example, a forehead or nose region) of the appearance image 420 of the subject 10, for example, a forehead or nose region of the appearance image 410. Various types of technologies for synchronizing the positions and orientations of two images may be used according to exemplary embodiments, and thus a detailed description thereof will be omitted here.

According to an exemplary embodiment, when the control apparatus 100 displays the fusion image 430, a user (for example, a radiotherapist) may identify both a facial expression change and a temperature change of the subject 10 at the same time based on the fusion image 430.

According to an exemplary embodiment, the user (for example, a radiotherapist) may control a fusion ratio of the fusion image 430 or respective transparency levels of the appearance image 410 and the temperature distribution image 420 of the subject 10 displayed on the screen. This will be described in greater detail with reference to FIGS. 5 and 6.

Figure 5:
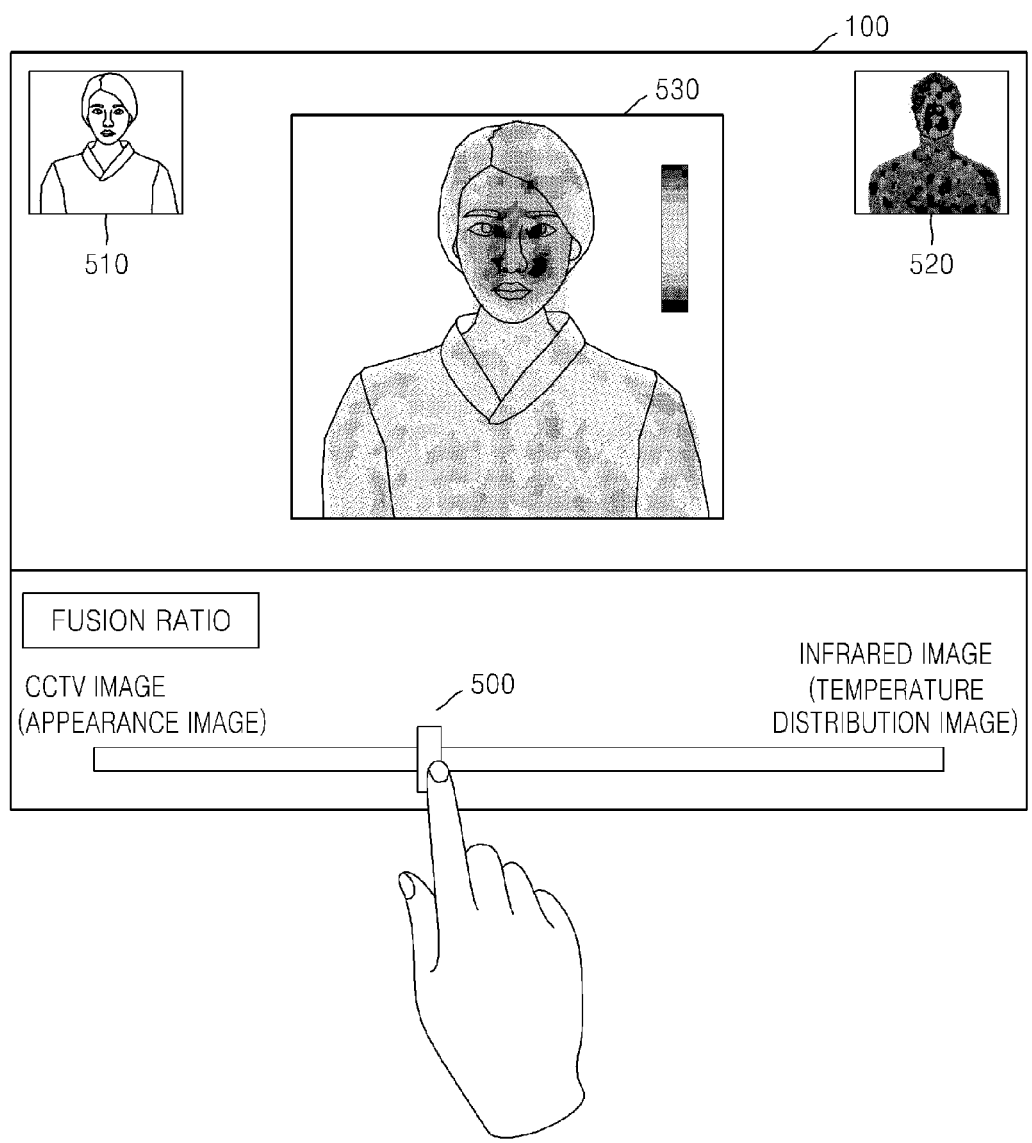
FIG. 5 is a diagram illustrating a graphical user interface (GUI) for inputting a fusion ratio, according to an exemplary embodiment.

FIG. 5 is a diagram illustrating a graphical user interface (GUI) for inputting a fusion ratio, according to an embodiment of the present invention.

Referring to FIG. 5, the control apparatus 100 may display a fusion image 530 of an appearance image 510 and a temperature distribution image 520 of the subject 10 on a screen. The control apparatus 100 may display an adjustment button for adjusting a fusion ratio of the appearance image 510 and the temperature distribution image 520 of the subject 10. The adjustment button 500 may be implemented as a button on a graphical user interface (GUI).

When the adjustment button 500 is dragged in a direction toward the appearance image 510, for example, to the left, the appearance image 510 in the fusion image 530 may be more prominent than the temperature distribution image 520. On the other hand, when the adjustment button 500 is dragged in a direction toward the temperature distribution image 520, for example, to the right, the temperature distribution image 520 in the fusion image 530 may be more prominent than the appearance image 510.

According to an exemplary embodiment, the user (for example, a radiotherapist) may drag the adjustment button 500 to the left or right to increase a display ratio of one of the appearance image 510 and the temperature distribution image 520 in the fusion image 430, according to the preference of the user.

Although the exemplary embodiment of FIG. 5 illustrates a slider bar as an example of the adjustment button 500 for adjusting a fusion ratio, exemplary embodiments are not limited thereto. For example, the control apparatus 100 may display an input window for inputting a fusion ratio of the appearance image 510 and the temperature distribution image 520. In this case, the user (for example, a radiotherapist) may input a fusion ratio of, for example, 2:3, of the appearance image 510 to the temperature distribution image 250 through the input window. The control apparatus 100 may display a fusion image 530 of the appearance image 510 and the temperature distribution image 520 in accordance with the fusion ratio input by the user (for example, a radiotherapist).

Figure 6:
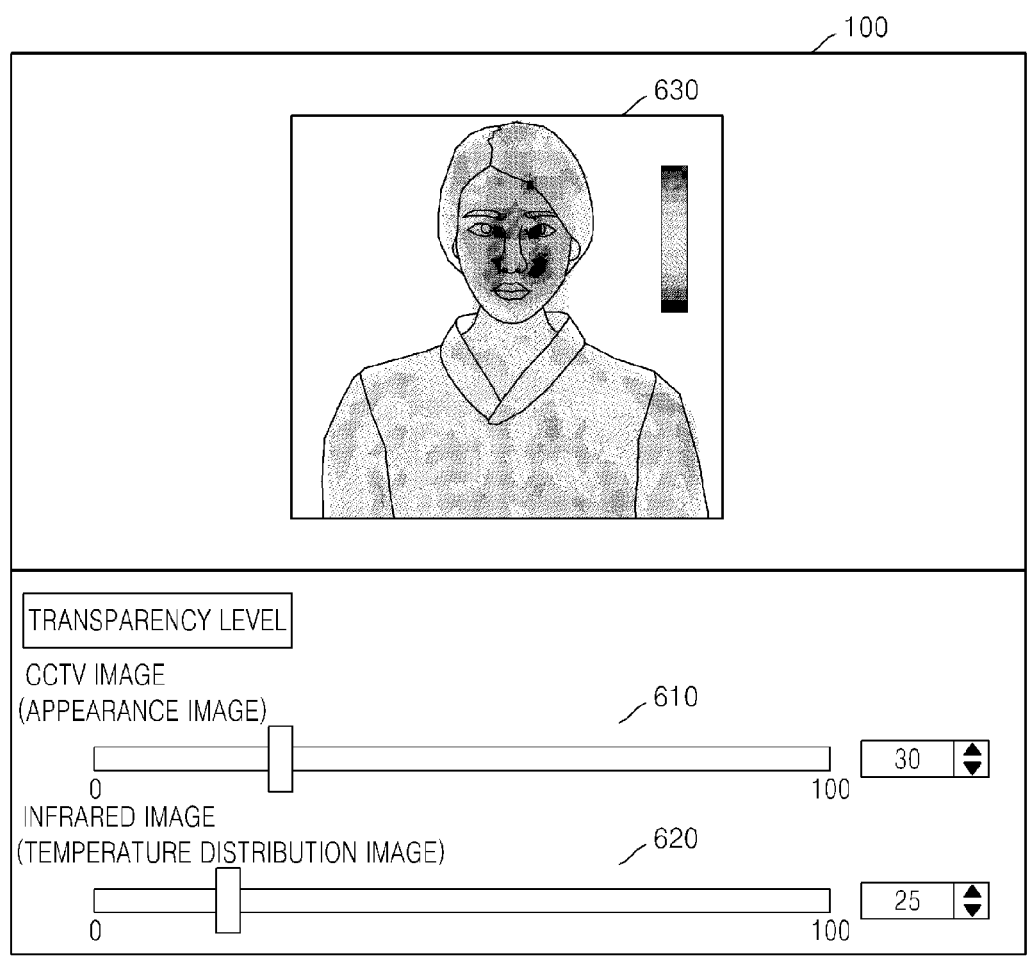
FIG. 6 is a diagram illustrating a GUI for adjusting respective transparency levels of an appearance image and a temperature distribution image of a subject, according to an exemplary embodiment.

FIG. 6 is a diagram illustrating a GUI for adjusting respective transparency levels of an appearance image and a temperature distribution image of a subject, according to an exemplary embodiment.

Referring to FIG. 6, the control apparatus 100 may display a fusion image 630 of an appearance image and a temperature distribution image of a subject on the screen. In this regard, the control apparatus 100 may display a first transparency button 610 for adjusting a transparency level of the appearance image, and a second transparency button 620 for adjusting a transparency level of the temperature distribution image. The first transparency button 610 and the second transparency button 620 may be implemented as buttons on a GUI.

When the first transparency button 610 is dragged to the left, the appearance image in the fusion image 630 may be more prominent than the temperature distribution image. On the other hand, when the first transparency button 610 is dragged to the right, the appearance image in the fusion image 630 may be less prominent than the temperature distribution image.

When the second transparency button 620 is dragged to the left, the temperature distribution image in the fusion image 630 may appear sharper than the appearance image. On the other hand, when the second transparency button 620 is dragged to the right, the temperature distribution image in the fusion image 630 may appear duller than the appearance image.

According to an exemplary embodiment, a user (for example, a radiotherapist) may adjust respective transparency levels of the appearance image and the temperature distribution image of the subject in the fusion image 630.

According to an exemplary embodiment, the user (for example, a radiotherapist) may define an interest region in the appearance image of the subject. This will be described in greater detail with reference to FIGS. 7 and 8.

Figure 7:
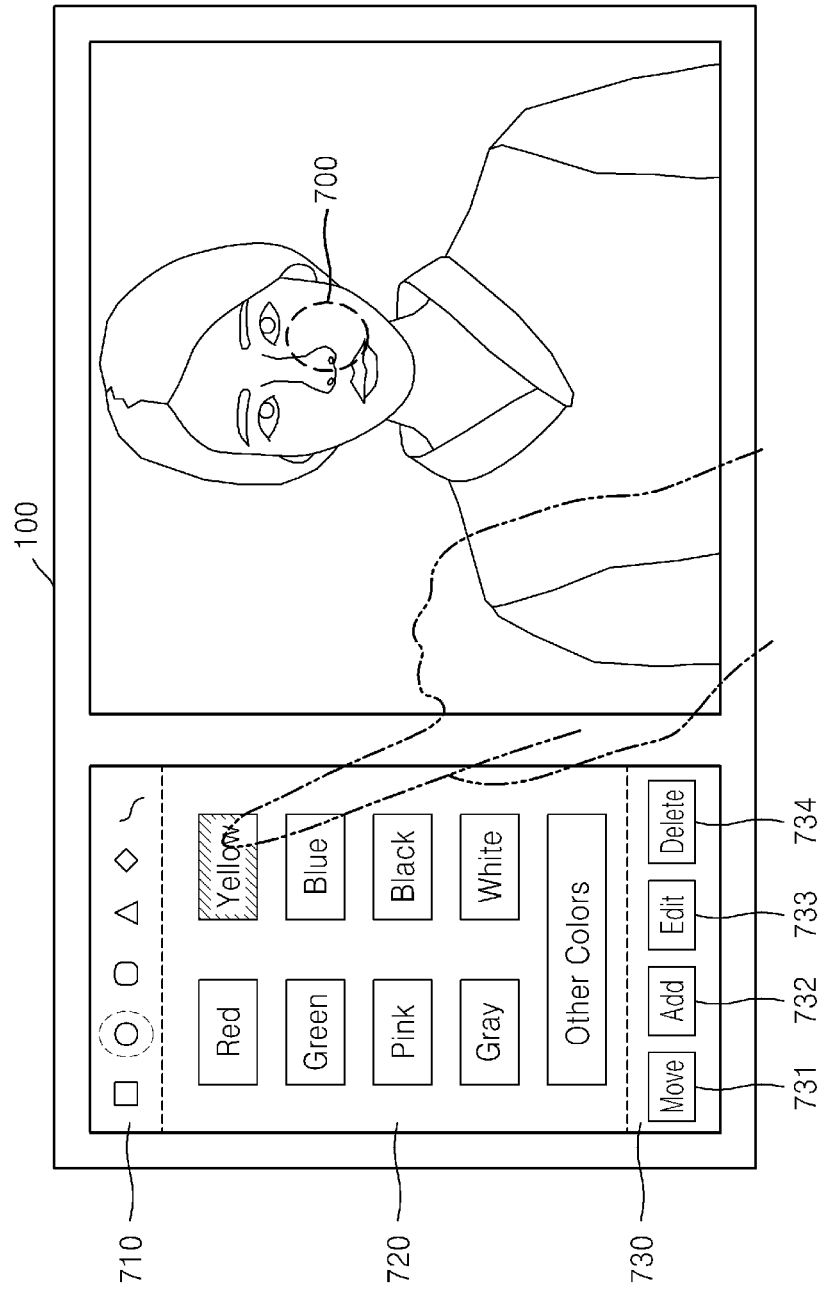
FIG. 7 is a diagram illustrating a GUI for defining an interest region, according to an exemplary embodiment.

FIG. 7 is a diagram illustrating a GUI for defining an interest region, according to an exemplary embodiment.

Referring to FIG. 7, according to an exemplary embodiment, the control apparatus 100 may provide a set-up window for defining an interest region 700. For example, the control apparatus 100 may provide a template list 710 for defining the interest region 700. A template may be a geometrical figure to define the interest region 700. According to an exemplary embodiment, the template list 710 may include a circle, a tetragon, a pentagon, and an adjustable shape.

For example, when a user (for example, a radiotherapist) selects a circle from the template list 710, the user may select the interest region 700 by changing the position and size of the circle on an appearance image of a subject.

According to an exemplary embodiment, the control apparatus 100 may provide a color list 720 for choosing which color is used to represent the interest region 700. According to an exemplary embodiment, the control apparatus 100 may provide a control panel 730 for controlling the interest region 700. According to an exemplary embodiment, the control panel 730 may include a move button 731 for changing the position of the interest region 700, an add button 732 for adding another interest region, an edit button 733 for editing the interest region 700, and a delete button 734 for deleting the interest region 700.

Figure 8:
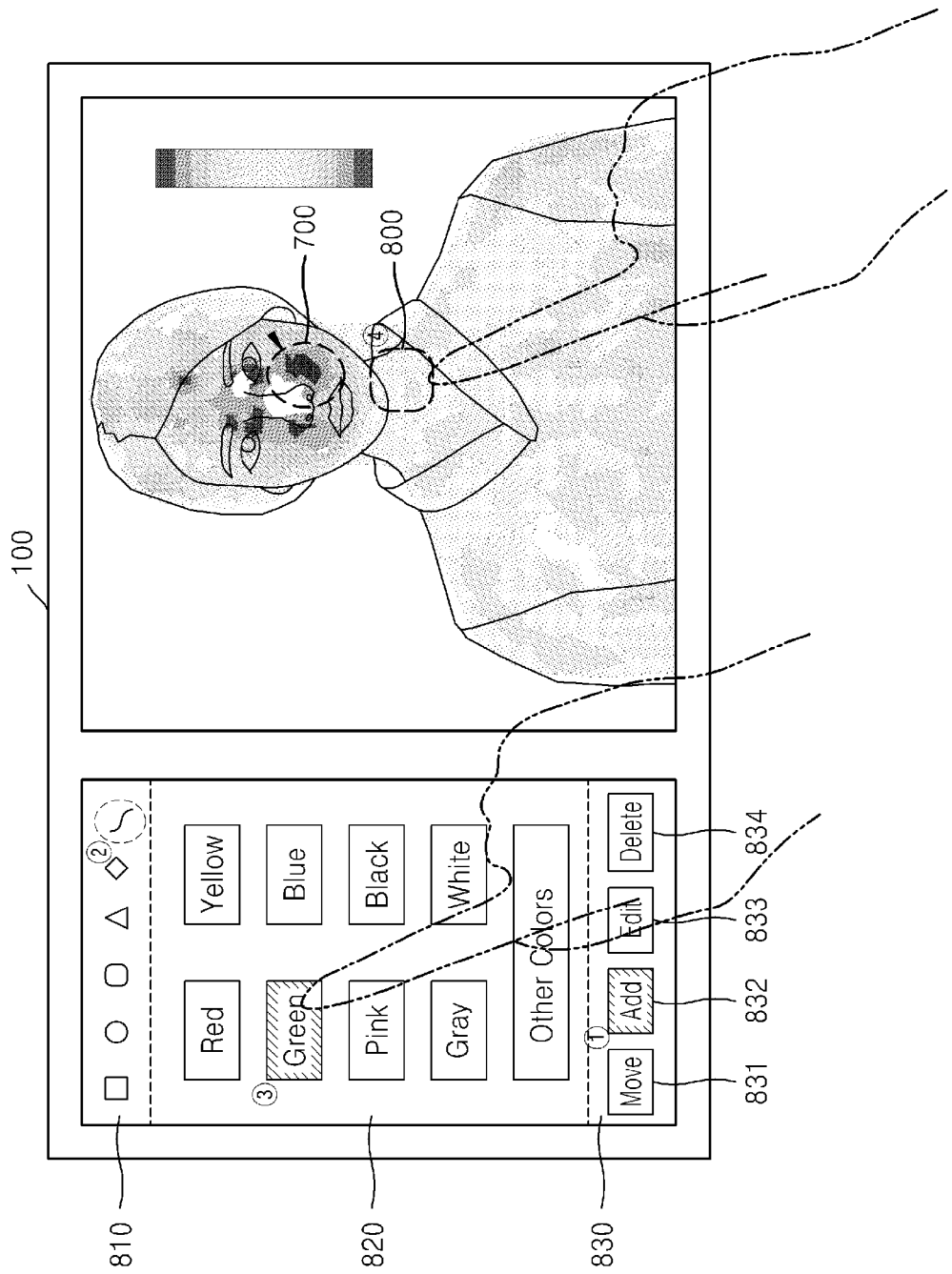
FIG. 8 is a diagram illustrating a GUI for defining a plurality of interest regions, according to an exemplary embodiment.

FIG. 8 is a diagram illustrating a GUI for defining a plurality of interest regions, according to an exemplary embodiment.

Referring to FIG. 8, a user (for example, a radiotherapist) may further define an interest region 800 on the fusion image in addition to the interest region 700 of FIG. 7. For example, the user (for example, a radiotherapist) may select an add button 832 on a control panel 830 (Operation ①), select a free curve from a template list 810 (Operation ②), and select "Green" color from a color list 820 (Operation ③).

In this case, the user (for example, a radiotherapist) may select the interest region 800 by drawing a green line on the fusion image of the subject with a touch tool (for example, a finger or an electronic stylus), a mouse, or a track ball.

According to an exemplary embodiment, when a contrast medium has been injected into the left arm of the subject, the user (for example, a radiotherapist) may select a region around the left carotid artery of the subject as the interest region 800 to rapidly determine whether or not a side effect of the contrast medium has occurred in the subject.

Hereinafter, a set-up window for inputting a reference temperature to be used in determining whether or not a side effect of the contrast medium has occurred in the subject, based on the temperature distribution image of the subject, according to an exemplary embodiment, will be described in greater detail with reference to FIG. 9.

Figure 9:
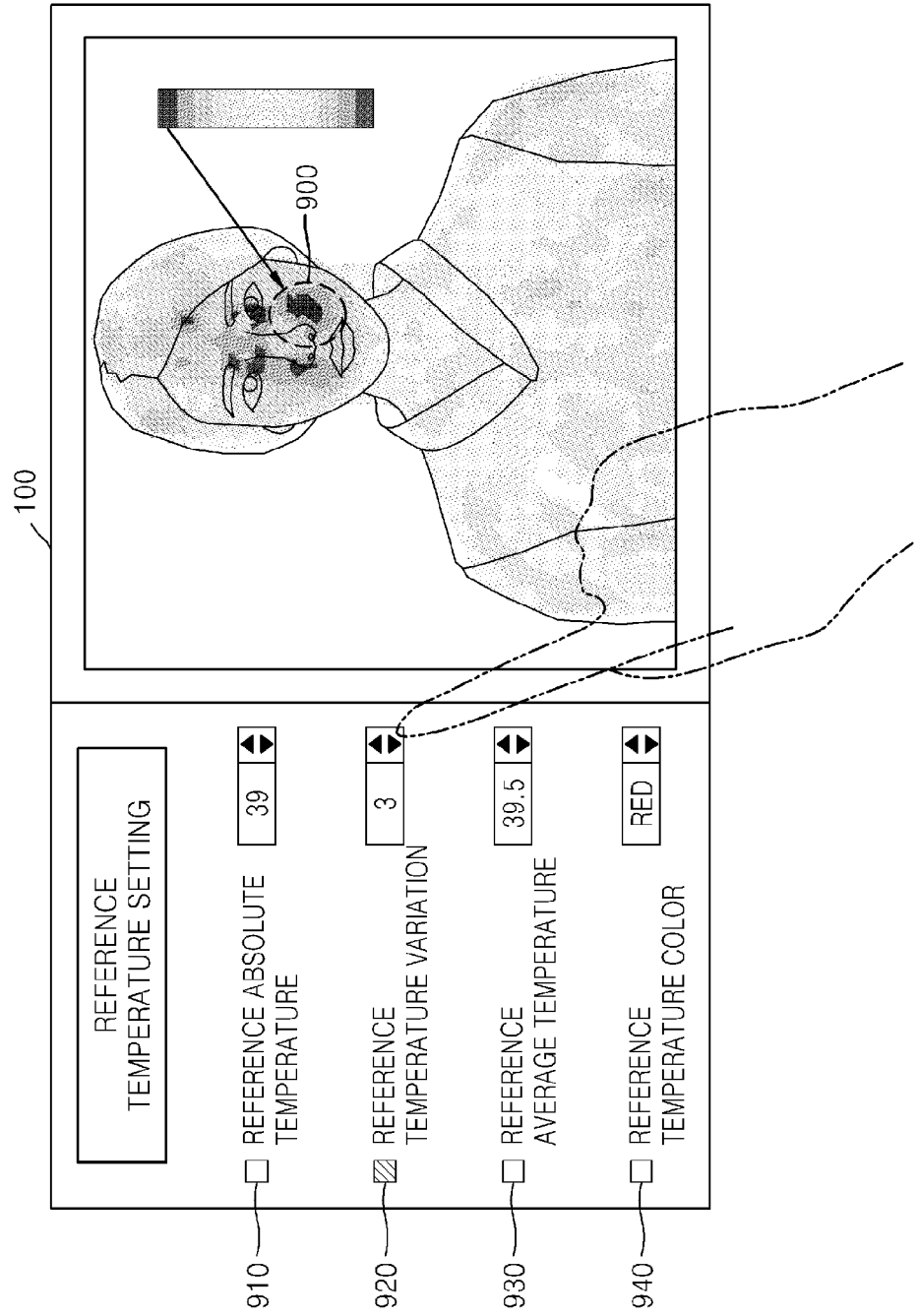
FIG. 9 is a diagram illustrating a GUI for inputting a reference temperature, according to an exemplary embodiment.

FIG. 9 is a diagram illustrating a GUI for inputting a reference temperature, according to an exemplary embodiment.

According to an exemplary embodiment, the control apparatus 100 may provide a set-up window for inputting a reference temperature. According to an exemplary embodiment, the reference temperature may be at least one of a reference absolute temperature 910, a reference temperature variation 920, a reference average temperature 930, and a reference temperature color 940.

According to an exemplary embodiment, a user (for example, a radiotherapist) may set a reference absolute temperature of, for example, 39° C., as the reference temperature. In this case, when a highest temperature of the subject in an interest region 900 is higher than the reference absolute temperature of 39° C., the control apparatus 100 may determine that a side effect of the contrast medium has occurred in the subject.

According to another exemplary embodiment, the user (for example, a radiotherapist) may set a reference temperature variation of, for example, 3° C., as the reference temperature. In this case, when an amount of temperature change of the subject in the interest region 900 is greater than the reference temperature variation of 3° C., the control apparatus 100 may determine that a side effect of the contrast medium has occurred in the subject has occurred in the subject.

According to another exemplary embodiment, the user (for example, a radiotherapist) may set a reference average temperature of, for example, 39.5° C., as the reference temperature. In this case, when an average temperature of the subject in the interest region 900 is higher than the reference average temperature of 39.5° C., the control apparatus 100 may determine that a side effect of the contrast medium has occurred in the subject.

According to another exemplary embodiment, the user (for example, a radiotherapist) may set a reference temperature color of red to indicate a temperature of 39° C. to 39.5° C. In this case, when a color of the interest region 900 changes to 'red', the control apparatus 200 determines that a side effect of the contrast medium has occurred in the subject.

Hereinafter, exemplary embodiments in which the control apparatus 100 selectively controls the medical diagnostic system 200 depending on whether or not a side effect of the contrast medium has occurred in the subject will be described in greater detail with reference to FIGS. 10 to 15.

Figure 10:
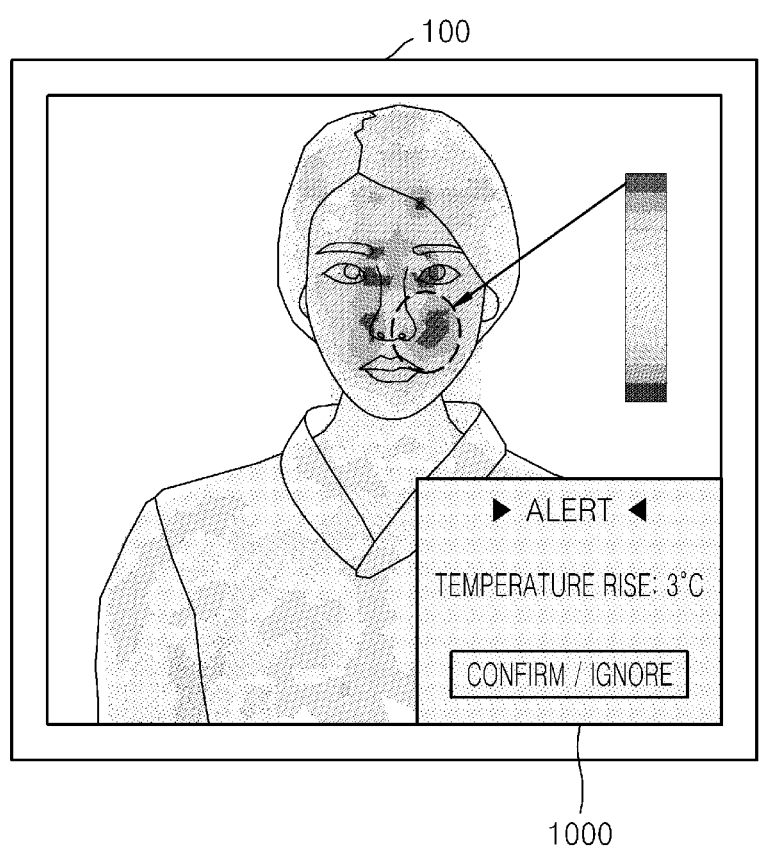
FIG. 10 is a diagram illustrating the provision of an alert message, according to an exemplary embodiment.

FIG. 10 is a diagram illustrating the provision of an alert message, according to an exemplary embodiment.

Referring to FIG. 10, the control apparatus 100 may output an alert window 1000 when it is determined that a side effect of the contrast medium has occurred in the subject. For example, when the body temperature of the subject changes from 36.5° C. before injection of the contrast medium to 39.5° C. after the injection of the contrast medium, the temperature change of 3° C. in an interest region is greater than a predefined reference temperature variation of, for example, 2.5° C., so the control apparatus 100 may output the alert window 1000. The alert window 1000 may display a current body temperature of the subject (for example, 39.5° C.) and information about an increase in body temperature (for example, 3° C.).

When the user (for example, a radiotherapist) selects a confirm button in the alert window 1000, the control apparatus 100 may display a control list for the medical diagnostic system 200. This will be described in greater detail with reference to FIG. 11.

Figure 11:
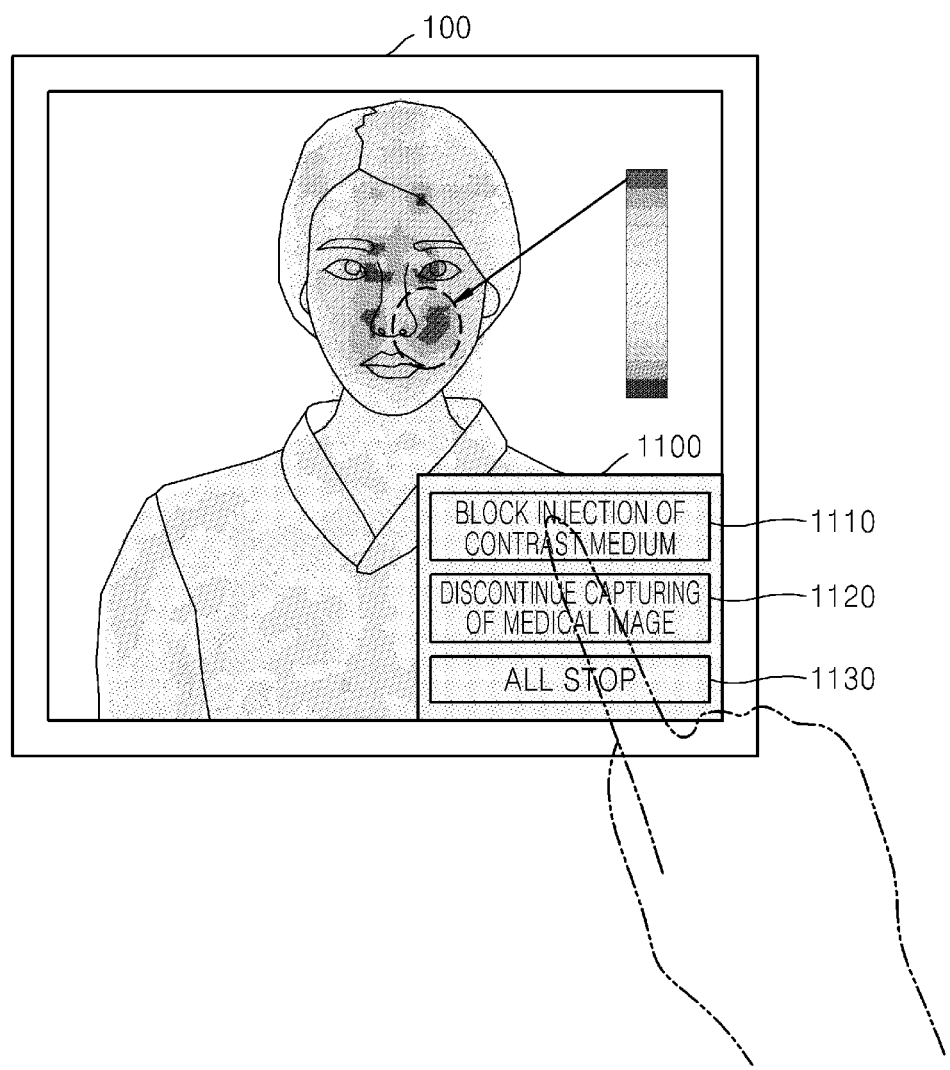
FIG. 11 is a diagram illustrating a GUI for providing a control list, according to an exemplary embodiment.

FIG. 11 is a diagram illustrating a GUI for providing a control list, according to an exemplary embodiment.

Referring to FIG. 11, according to an exemplary embodiment, the control apparatus 100 may display a control list 1100 on the screen when it is determined that a side effect of the contrast medium has occurred in the subject, the control list 1100 including at least one of a button 1110 for blocking injection of the contrast medium, a button 1120 for discontinuing capturing of a medical image of the subject, and a button 1130 for blocking the injection of the contrast medium and simultaneously discontinuing capturing of a medical image of the subject.

When a user (for example, a radiotherapist) selects the button 1110 for blocking the injection of the contrast medium from the control list 1100, the control apparatus 100 may block the injection of the contrast medium by transmitting a control command, in accordance with a control protocol of the contrast medium injection device 220, to the contrast medium injection device 220.

When a user (for example, a radiotherapist) selects the button 1120 for discontinuing capturing of a medical image of the subject from the control list 1100, the control apparatus 100 may discontinue capturing the medical image of the subject by transmitting a control command, in accordance with a control protocol of the medical image acquisition device 210, to the medical image acquisition device 210.

The control apparatus 100 may provide the button 1130 that allows the user (for example, a radiotherapist) to block the injection of the contrast medium and simultaneously discontinue capturing a medical image of the subject. This will be descried in greater detail with reference to FIG. 12.

Figure 12:
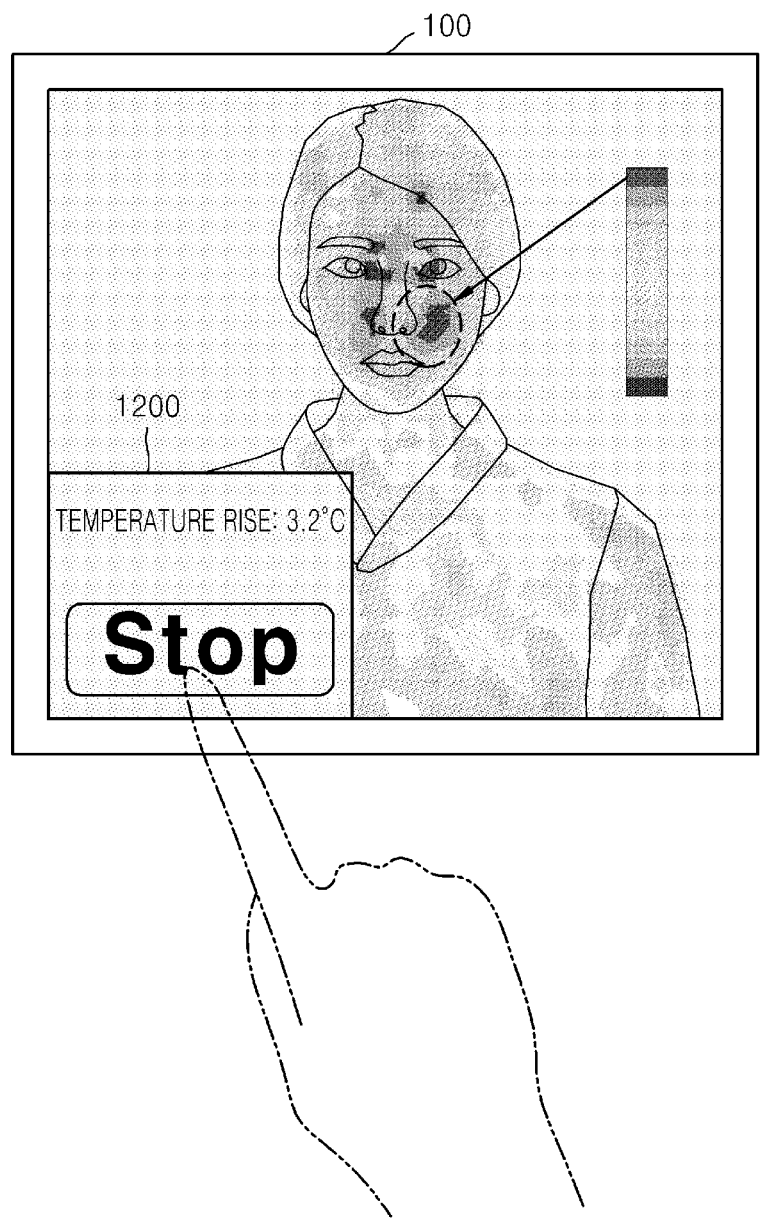
FIG. 12 is a diagram illustrating a GUI for blocking injection of the contrast medium and simultaneously discontinuing capturing of a medical image, according to an exemplary embodiment.

FIG. 12 is a diagram illustrating a GUI for blocking the injection of the contrast medium and simultaneously discontinuing capturing of a medical image, according to an exemplary embodiment.

Referring to FIG. 12, according to an exemplary embodiment, the control apparatus 100 may provide a Stop button 1200 for blocking the injection of the contrast medium and simultaneously discontinuing capturing of a medical image of the subject when it is determined that a side effect of the contrast medium has occurred in the subject. For example, when an amount of temperature change of, for example, 3.2° C., in an interest region is greater than a predefined reference temperature variation of, for example, 3° C., the control apparatus 100 may provide the Stop button 1200 along with information about the temperature change of 3.2° C. in the interest region.

When a user (for example, a radiotherapist) selects the Stop button 1200, the control apparatus 100 may transmit a control command for blocking the injection of the contrast medium to the contrast medium injection device 220 and a control command for discontinuing capturing of a medical image to the medical image acquisition device 210.

Although the exemplary embodiment of FIG. 12 exemplarily describes the Stop button 1200 as being implemented as a GUI button, exemplary embodiments of are not limited thereto. For example, the Stop button 1200 may be a physical button attached to the control apparatus 100.

Figure 13:
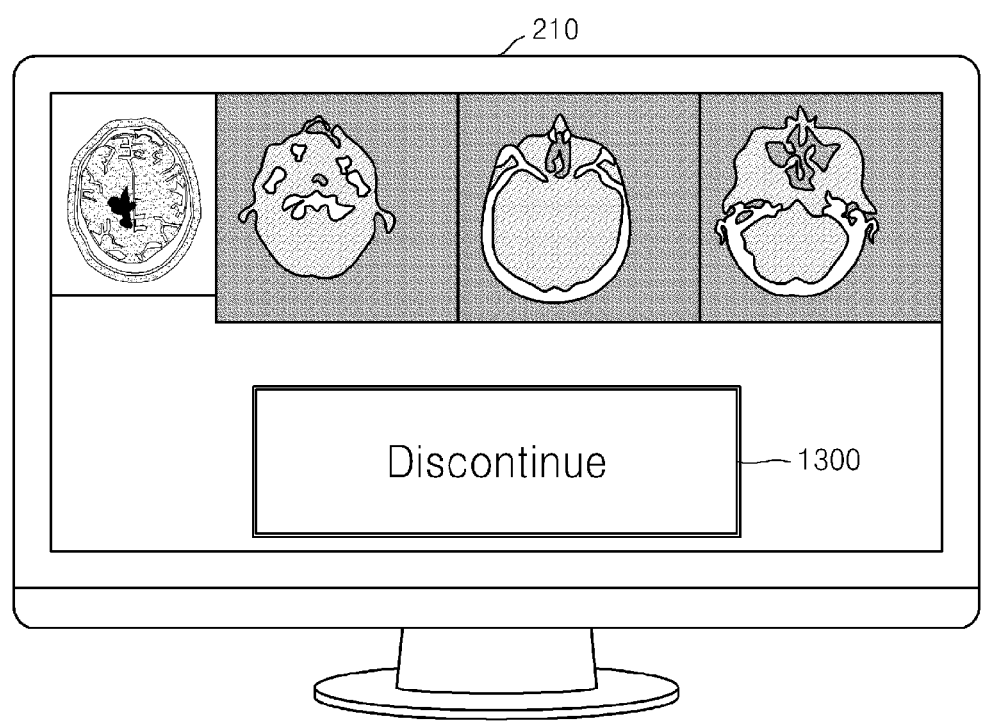
FIG. 13 is a diagram illustrating a GUI for discontinuing capturing of a medical image, according to an exemplary embodiment.

FIG. 13 is a diagram illustrating a GUI for discontinuing capturing of a medical image, according to an exemplary embodiment of the present invention.

Referring to FIG. 13, the medical image acquisition device 210 may receive a control command for discontinuing capturing of a medical image from the control apparatus 100, and discontinue capturing the medical image according to the control command.

The medical image acquisition device 210 may also display an object 1300 (for example, a text or an image) indicating an interruption of capturing the medical image on the screen.

Figure 14:
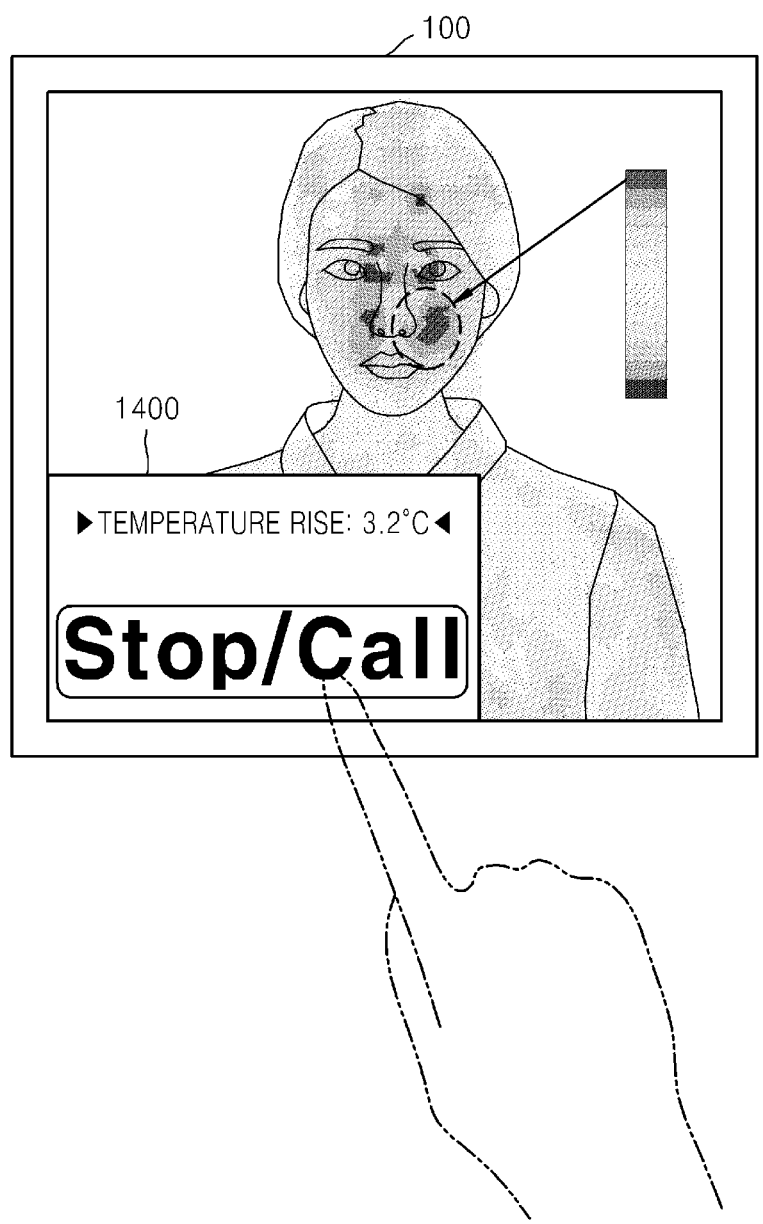
FIG. 14 is a diagram illustrating a GUI for a voice call, according to an exemplary embodiment.

FIG. 14 is a diagram illustrating a GUI for initiating a voice call, according to an exemplary embodiment.

Referring to FIG. 14, according to an exemplary embodiment, the control apparatus 100 may display a communication window 1400 for requesting a predefined external terminal to initiate a voice connection, or transmitting a notification message to the predefined external terminal when it is determined a side effect of the contrast medium has occurred in the subject.

For example, when an amount of temperature change of, for example, 3.2° C. in the interest region is greater than a predefined reference temperature of, for example, 3° C., the control apparatus 100 may provide a Call button along with information about the temperature change of 3.2° C. in the interest region.

According to an exemplary embodiment, when a user (for example, a radiotherapist) selects the Call button, the control apparatus 100 may request a predefined external terminal (for example, a doctor's terminal) to initiate a voice connection or may transmit a notification message related to the occurrence of a side effect of the contrast medium in the subject to the predefined external terminal (for example, the doctor's terminal).

According to another exemplary embodiment, when the user (for example, a radiotherapist) selects the Call button, the control apparatus 100 may provide a terminal list of connectable terminals, and the user may select a terminal from the terminal list.

FIG. 15 is a diagram for describing a technique of adjusting an angle of a table of a medical image acquisition device, according to an exemplary embodiment.

Referring to FIG. 15, according to an exemplary embodiment, the control apparatus 100 may transmit a control command for adjusting an angle of a table 1500 on which a subject lies down, to the medical image acquisition device 210 when it is determined that a side effect of the contrast medium has occurred in the subject.

The medical image acquisition device 210 may adjust an angle of the table 1500 on which the subject lies down, according to the control command received from the control apparatus 100. For example, when it is determined that a side effect of the contrast medium has occurred in the subject, the control apparatus 100 may adjust an angle of the table 1500 such that the upper body of the subject is raised while the lower body of the subject is lowered.

Figure 16:
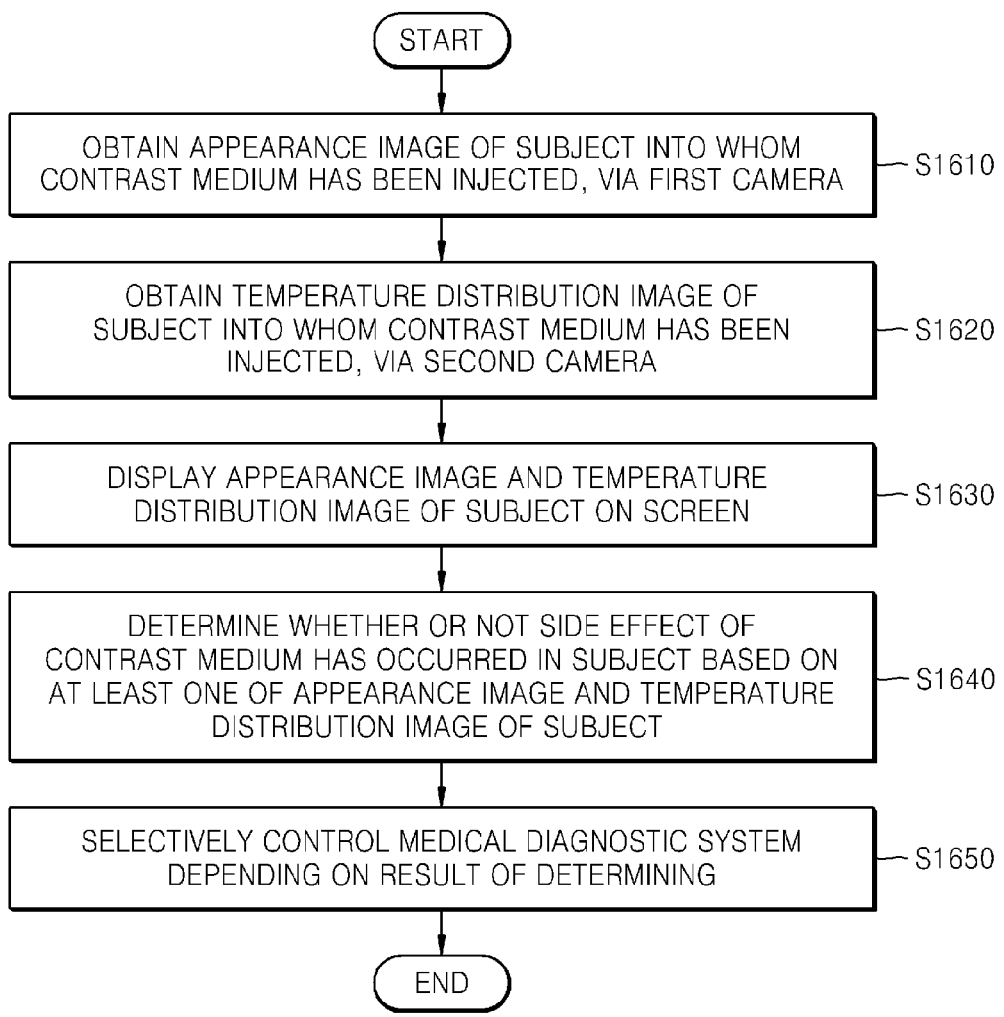
FIG. 16 is a flowchart of a method of controlling a medical diagnostic system based on at least one of an appearance image and a temperature distribution image of a subject, according to an exemplary embodiment.

FIG. 16 is a flowchart of a method of controlling a medical diagnostic system based on at least one of an appearance image and a temperature distribution image of a subject, according to an exemplary embodiment.

In operation S1610, the control apparatus 100 may obtain an appearance image of a subject into whom a contrast medium has been injected, via the first camera 111.

According to an exemplary embodiment, the appearance image of the subject may include information about a facial expression change of the subject. According to an exemplary embodiment, the appearance image of the subject may be a 2-dimensional image or a 3-dimensional image. According to an exemplary embodiment, the appearance image of the subject may be a real-time image obtained beginning from the injection of the contrast medium into a blood vessel or tissue of the subject. Operation S1610 corresponds to operation S210 of FIG. 2 described above, and thus a detailed description thereof will be omitted.

In operation S1620, the control apparatus 100 may obtain a temperature distribution image of the subject into whom the contrast medium has been injected, via the second camera 112.

According to an exemplary embodiment, the control apparatus 100 may express the temperature distribution image in various forms by mapping the body temperature of the subject to colors, contrasts, patterns, contours, or other variables.

According to an exemplary embodiment, the temperature distribution image of the subject may be a real-time image obtained beginning from the injection of the contrast medium into a blood vessel or tissue of the subject. Operation S1620 corresponds to operation S220 of FIG. 2 described above, and thus a detailed description thereof will be omitted.

In operation S1630, the control apparatus 100 may display the appearance image and the temperature distribution image of the subject on the screen. According to an exemplary embodiment, the control apparatus 100 may display the appearance image and the temperature distribution image of the subject in different regions on the screen.

In operation S1640, the control apparatus 100 may determine whether or not a side effect of the contrast medium has occurred in the subject based on at least one of the appearance image and the temperature distribution image of the subject.

According to an exemplary embodiment, the control apparatus 100 may analyze a facial expression change of the subject based on the appearance image of the subject in the fusion image. The control apparatus 100 may determine whether or not a side effect of the contrast medium has occurred in the subject based on the facial expression change of the subject. For example, the control apparatus 100 may measure a facial expression change rate of the subject and compare the measured facial expression change rate of the subject with a predefined reference facial expression change rate (for example, 20%). When the measured facial expression change rate of the subject is greater than a predefined reference facial expression change rate of, for example, 20%, the control apparatus 100 may determine that a side effect of the contrast medium has occurred in the subject.

According to another exemplary embodiment, the control apparatus 100 may determine a temperature change of the subject based on the temperature distribution image of the subject in a fusion image. The control apparatus 100 may determine whether a side effect of the contrast medium has occurred in the subject based on the temperature change of the subject.

For example, the control apparatus 100 may determine whether or not a side effect of the contrast medium has occurred in the subject based on a result of comparing an amount of temperature change of the subject with a predefined amount of temperature change of, for example, about 3° C. According to an exemplary embodiment, the control apparatus 100 may determine whether or not a side effect of the contrast medium has occurred in the subject based on a result of comparing a temperature change of the subject with a predefined reference temperature of, for example, 39° C.

According to an exemplary embodiment, the control apparatus 100 may determine whether or not a side effect of the contrast medium has occurred in the subject, based on a temperature change in an interest region. The interest region may be automatically defined by the control apparatus 100 or manually by a user, for example, a radiotherapist. According to exemplary embodiments, one interest region or at least two interest regions may be defined.

According to an exemplary embodiment, the control apparatus 100 may determine whether or not a side effect of the contrast medium has occurred in the subject based on a facial expression change of the subject or a temperature change of the subject based on a comparison before and after the injection of the contrast medium.

In operation S1650, the control apparatus 100 may selectively control the medical diagnostic system 200 depending on a result of the determining whether or not a side effect of the contrast medium has occurred in the subject.

According to an exemplary embodiment, the control apparatus 100 may control the contrast medium injection device 220 for injecting a contrast medium into a subject. For example, the control apparatus 100 may control the contrast medium injection device 220 to block the injection of the contrast medium when it is determined that a side effect of the contrast medium has occurred in the subject.

According to an exemplary embodiment, the control apparatus 100 may control the medical image acquisition device 210 to discontinue capturing a medical image of the subject when it is determined that a side effect of the contrast medium has occurred in the subject.

According to an exemplary embodiment, the control apparatus 100 may display at least one of a button for blocking injection of the contrast medium and a button for discontinuing capturing of a medical image of the subject on the screen when it is determined that a side effect of the contrast medium has occurred in the subject. According to another exemplary embodiment, the control apparatus 100 may display a button for blocking the injection of the contrast medium and simultaneously discontinuing capturing of a medical image of the subject on the screen when it is determined that a side effect of the contrast medium has occurred in the subject.

The control apparatus 100 may transmit a control command for blocking injection of the contrast medium to the contrast medium injection device 220 or transmit a control command for discontinuing capturing of a medical image of the subject of the medical image acquisition device 210, when a user's selection of the button is input. In this regard, according to an exemplary embodiment, the control apparatus 100 may generate a control command according to a control protocol of the medical image acquisition device 210 or the contrast medium injection device 220.

According to an exemplary embodiment, the control apparatus 100 may output an alarm signal when it is determined that a side effect of the contrast medium has occurred in the subject. The alarm signal may include at least one of a video signal, an audio signal, and a vibration signal. For example, when an amount of temperature change of the subject in the interest image is greater than a predefined reference temperature variation, the control apparatus 100 may output an alarm signal.

According to an exemplary embodiment, the control apparatus 100 may request a preselected external terminal 230 to initiate a voice connection or transmit a notification message to the preselected external terminal 230 when it is determined that a side effect of the contrast medium has occurred in the medium. For example, the control apparatus 100 may request a doctor's terminal or a nurse's terminal to initiate a voice connection when a side effect of the contrast medium has occurred in the subject and is considered to be an emergency.

According to an exemplary embodiment, the control apparatus 100 may control an angle of a table of the medical image acquisition device 210. For example, the control apparatus 100 may control an angle of the table of the medical image acquisition device 210 to help the subject sit upright when it is determined that a side effect of the contrast medium has occurred in the subject.

Figure 17:
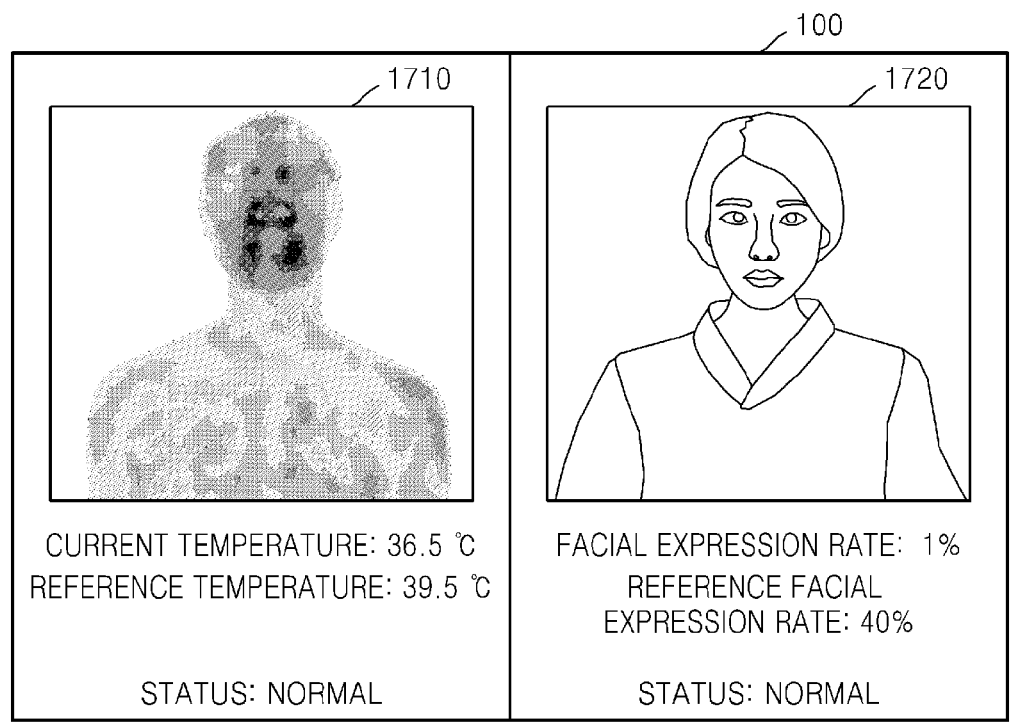
FIG. 17 is a diagram illustrating a GUI displaying an appearance image and a temperature distribution image of a subject, according to an exemplary embodiment.

FIG. 17 is a diagram illustrating a GUI displaying an appearance image and a temperature distribution image of a subject, according to an exemplary embodiment.

Referring to FIG. 17, according to an exemplary embodiment, the control apparatus 100 may display a temperature distribution image of a subject in a first region 1710 of the screen, and an appearance image of the subject in a second region 1720.

According to an exemplary embodiment, the control apparatus 100 may display about information of a current body temperature of the subject (for example 36.5° C.) and reference temperature information (for example, 39.5° C.), as a reference to be used in determining whether or not a side effect of the contrast medium has occurred in the subject, in the first region 1710.

According to an exemplary embodiment, the control apparatus 100 may display a facial expression change rate of the subject (for example, 1%) and a reference facial expression change rate (for example, 40%), as a reference to be used in determining whether or not a side effect of the contrast medium has occurred in the subject, in the second region 1720. According to an exemplary embodiment, the control apparatus 100 may display a numerical value or a geometrical figure to indicate a likelihood that a side effect of the contrast medium may occur.

Figure 18:
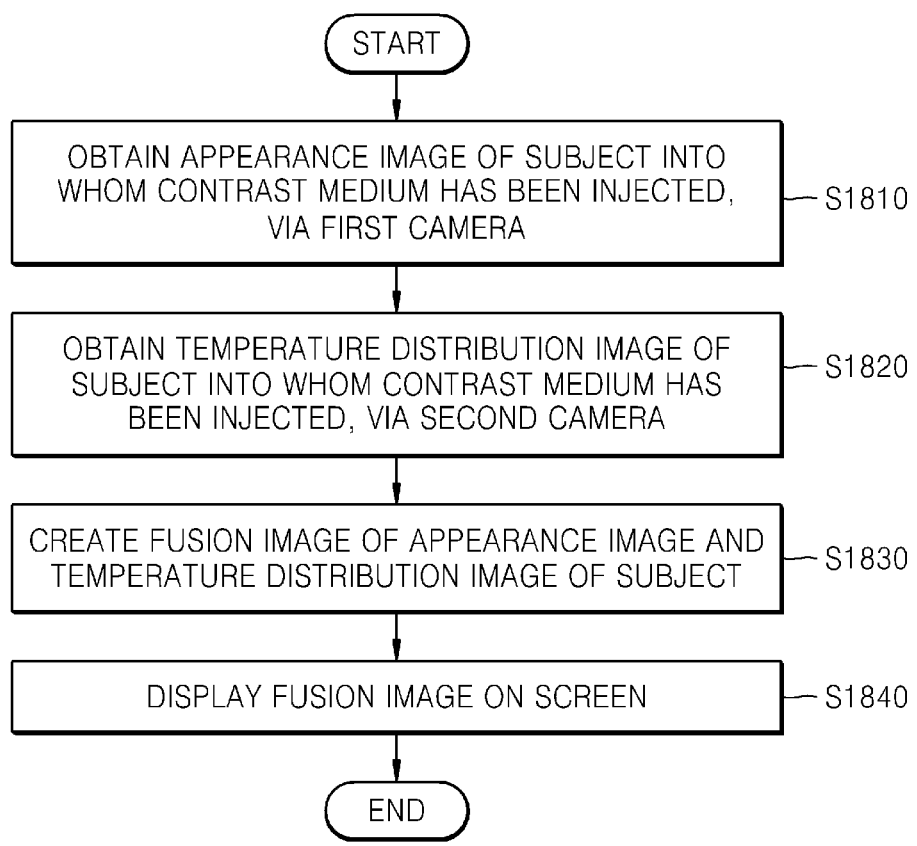
FIG. 18 is a flowchart of a method of providing a subject's image, according to an exemplary embodiment.

FIG. 18 is a flowchart of a method of providing a subject's image, according to an exemplary embodiment.

In operation S1810, according to an exemplary embodiment, the control apparatus 100 may obtain an appearance image of a subject via the first camera 111. In operation S1820, the control apparatus 100 may obtain a temperature distribution image of the subject via the second camera 112. Operations S1810 and S1820 correspond to operations S210 and S220 of FIG. 2, respectively, and thus detailed descriptions thereof will be omitted.

In operation S1830, the control apparatus 100 may create a fusion image of the appearance image and the temperature distribution image of the subject.

According to an exemplary embodiment, the control apparatus 100 may display a set-up window for inputting respective transparency levels of the appearance image and the temperature distribution image of the subject. The control apparatus 100 may receive an input of the respective transparency levels of the appearance image and the temperature distribution image of the subject via the set-up window. The control apparatus 100 may create the fusion image of the appearance image and the temperature distribution image of the subject based on the input of the respective transparency levels. This is described above with reference to FIGS. 5 and 6, and a detailed description thereof will be omitted.

In operation S1840, the control apparatus 100 may display the fusion image on a screen. According to an exemplary embodiment, a user controls respective transparency levels of the appearance image and the temperature distribution image of the subject, and the fusion image in which the controlled transparency levels are reflected may be displayed on the screen.

According to an exemplary embodiment, the control apparatus 100 may receive a user's input by which a region of the displayed fusion image is selected as an interest region.

Figure 19:
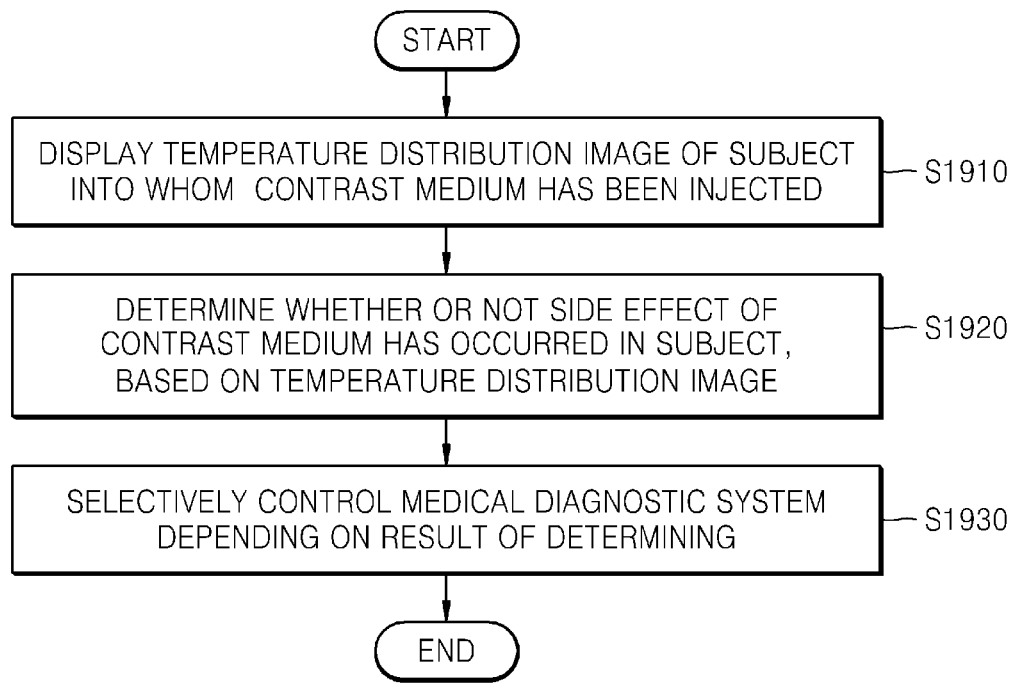
FIG. 19 is a flowchart of a method of controlling a medical diagnostic system based on a temperature distribution image of a subject, according to an exemplary embodiment.

FIG. 19 is a flowchart of a method of controlling a medical diagnostic system based on a temperature distribution image of a subject, according to an exemplary embodiment.

In operation S1910, the control apparatus 100 may display a temperature distribution image of a subject into whom a contrast medium has been injected. According to an exemplary embodiment, the control apparatus 100 may obtain a temperature distribution image of the subject into which the contrast medium has been injected, via the second camera 112, and display the obtained temperature distribution image of the subject on a screen. According to an exemplary embodiment, the control apparatus 100 may use at least one from among colors, contrasts, patterns, and contours when displaying the temperature distribution image in various forms.

In operation S1920, the control apparatus 100 may determine whether or not a side effect of the contrast medium has occurred in the subject based on the temperature distribution image. According to an exemplary embodiment, the control apparatus 100 may analyze a temperature change of the subject based on the temperature distribution image of the subject. The control apparatus 100 may determine whether or not a side effect of the contrast medium has occurred in the subject based on the temperature change of the subject.

For example, the control apparatus 100 may determine whether or not a side effect of the contrast medium has occurred in the subject based on a result of comparing an amount of temperature change of the subject with a predefined amount of temperature change of, for example, about 3° C. That is, when an amount of temperature change of the subject is greater than a predefined amount of temperature change of, for example, about 3° C., the control apparatus 100 may determine that a side effect of the contrast medium has occurred in the subject. On the other hand, when an amount of temperature change of the subject is less than a predefined amount of temperature change of, for example, about 3° C., the control apparatus 100 may determine that no side effect of the contrast medium has occurred in the subject.

In operation S1930, the control apparatus 100 may selectively control the medical diagnostic system 200 depending on a result of the determining whether or not a side effect of the contrast medium has occurred in the subject.

According to an exemplary embodiment, the control apparatus 100 may control the contrast medium injection device 220 for injecting a contrast medium into a subject. For example, the control apparatus 100 may control the contrast medium injection device 220 to block the injection of the contrast medium when it is determined that a side effect of the contrast medium has occurred in the subject.

According to an exemplary embodiment, the control apparatus 100 may control the medical image acquisition device 210 to discontinue capturing a medical image of the subject when it is determined that a side effect of the contrast medium has occurred in the subject.

Operation S1930 corresponds to operation S250 of FIG. 2 described above, and a detailed description thereof will be omitted.

Figure 20:
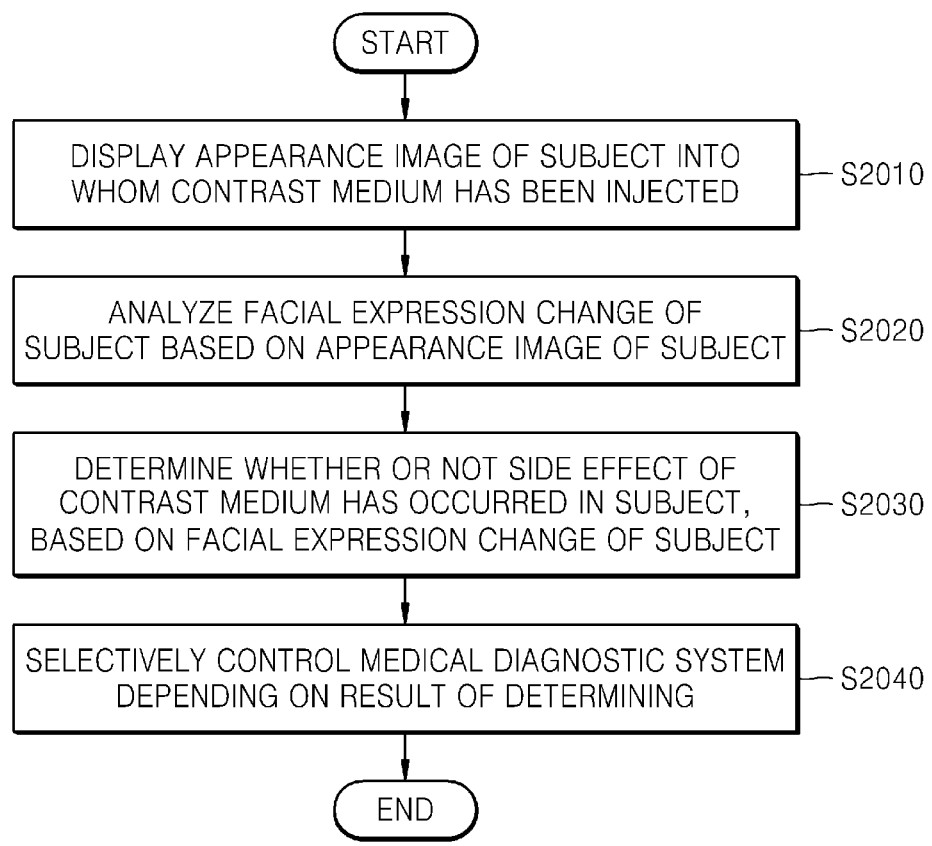
FIG. 20 is a flowchart of a method of controlling a medical diagnostic system based on an appearance image of a subject, according to an exemplary embodiment.

FIG. 20 is a flowchart of a method of controlling a medical diagnostic system based on an appearance image of a subject, according to an exemplary embodiment.

In operation S2010, the control apparatus 100 may display an appearance image of a subject into whom a contrast medium has been injected. According to an exemplary embodiment, the control apparatus 100 may obtain an appearance image of the subject into whom the contrast medium has been injected via the first camera 111 and display the obtained appearance image of the subject on a screen.

In operation S2020, the control apparatus 100 may analyze a facial expression change of the subject based on the appearance image of the subject. In operation S2030, the control apparatus 100 may determine whether or not a side effect of the contrast medium has occurred in the subject based on the facial expression change of the subject.

For example, the control apparatus 100 may measure a facial expression change rate of the subject and compare the measured facial expression change rate of the subject with a predefined reference facial expression change rate (for example, 30%). When the measured facial expression change rate of the subject is greater than a predefined reference facial expression change rate of, for example, 30%, the control apparatus 100 may determine that a side effect of the contrast medium has occurred in the subject.

In operation S2040, the control apparatus 100 may selectively control the medical diagnostic system 200 depending on a result of the determining whether or not a side effect of the contrast medium has occurred in the subject.

According to an exemplary embodiment, the control apparatus 100 may control the contrast medium injection device 220 for injecting a contrast medium into a subject. For example, the control apparatus 100 may control the contrast medium injection device 220 to block the injection of the contrast medium when it is determined that a side effect of the contrast medium has occurred in the subject.

According to an exemplary embodiment, the control apparatus 100 may control the medical image acquisition device 210 to discontinue capturing a medical image of the subject when it is determined that a side effect of the contrast medium has occurred in the subject.

Operation S2040 corresponds to operation S250 of FIG. 2 described above, and thus a detailed description thereof will be omitted. Hereinafter, structures of the control apparatus 100, according to exemplary embodiments, will be described in greater detail.

Figure 21:
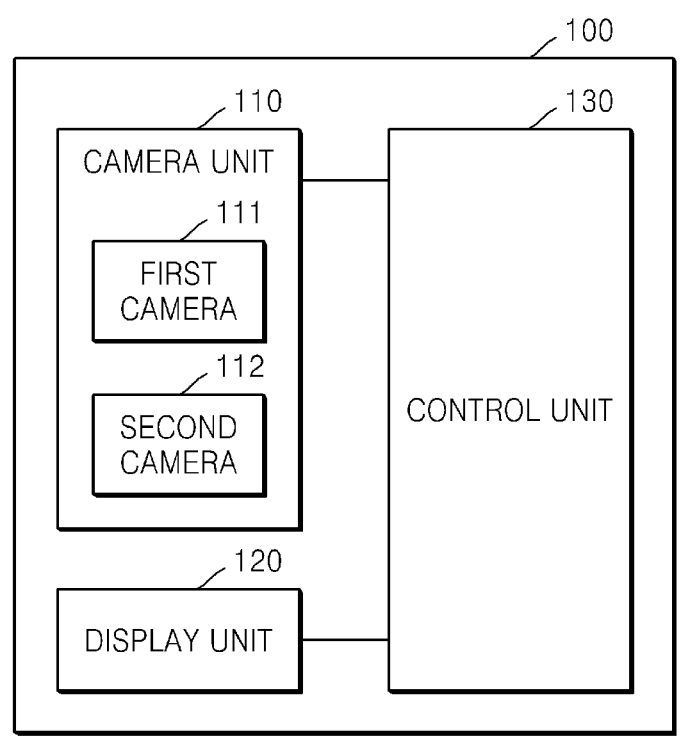
FIG. 21 is a block diagram of a medical diagnostic system control apparatus according to an exemplary embodiment.

FIG. 21 is a block diagram of a medical diagnostic system control apparatus (also referred to as a control apparatus 100) according to an exemplary embodiment.

Referring to FIG. 21, the control apparatus 100 may include a camera unit 110, a display unit 120, and a control unit 130. These elements of the control apparatus 100 in FIG. 21 are not essential. For example, the control apparatus 100 may be implemented with more or less elements than those illustrated in FIG. 21.

Hereinafter, the elements of the control apparatus 100 will be described in greater detail.

The camera unit 110 may obtain an image frame of, for example, a still image or a moving image, via an image sensor. The image captured by the image sensor may be processed by the control unit 130 or an image processing unit (not shown). The processed image frame (or series of frames) may be displayed on the display unit 120. The process image frame may be stored in a memory (not shown) or may be externally transmitted via a communication unit (not shown). The camera unit 110 may include at least two cameras according to a structure of the control apparatus 100. For example, the camera unit 110 may include a first camera 111 and a second camera 112.

The first camera 111 may capture an appearance image of a subject. Non-limiting examples of the first camera 111 include a CCTV camera and a webcam.

The second camera 112 may capture a temperature distribution image of the subject into whom a contrast medium has been injected. A non-limited example of the second camera 112 is an infrared camera.

According to an exemplary embodiment, the first camera 111 and the second camera 112 may be integrated as one camera or implemented as separate cameras.

The display unit 120 may display and output information processed in the control apparatus 100. According to an exemplary embodiment, the display unit 120 may display at least one of the appearance image of the subject, the temperature distribution image of the subject, and a fusion image of the appearance image and the temperature distribution image of the subject, and may also display a graphical user interface or GUI related to a control panel.

For example, the display unit 120 may display a set-up window for inputting respective transparency levels of the appearance image and the temperature distribution image of the subject on a screen. The display unit 120 may display at least one of a button for blocking the injection of the contrast medium and a button for discontinuing capturing a medical image of the subject when it is determined that a side effect of the contrast medium has occurred in the subject. According to another exemplary embodiment, the display unit 120 may display a button for blocking the injection of the contrast medium and simultaneously discontinuing capturing of a medical image of the subject on the screen when it is determined that a side effect of the contrast medium has occurred in the subject.

According to an exemplary embodiment, the display unit 120 may provide a set-up window for defining an interest region in the appearance image or in the fusion image of the subject. The display unit 120 may provide a set-up window for inputting a reference temperature used in determining whether or not a side effect of the contrast medium has occurred in the subject. According to an exemplary embodiment, the display unit 120 may display an alert window (for example, an alert message) when it is determined that a side effect of the contrast medium has occurred in the subject.

When the display unit 120 has a touch screen structure in which the display unit 120 forms a layered structure with a touch pad, the display unit 120 may serve both as an output device and an input device. The display unit 120 may include at least one of a liquid crystal display, a thin film transistor-liquid crystal display, an organic light-emitting diode display, a flexible display, a 3-dimensional (3D) display, and an electrophoretic display. The control apparatus 100 may include at least two display units 120 depending on an implemented structure thereof.

The control unit 130 may control the overall operation of the control apparatus 100. For example, the control unit 130 may control the overall operations of the cameral unit 110 and the display unit 120.

For example, the control unit 130 may analyze a facial expression change of the subject based on the appearance image of the subject, and determine whether or not a side effect of the contrast medium has occurred in the subject based on the facial expression change of the subject.

The control unit 130 may analyze a temperature change of the subject based on the temperature distribution image of the subject, and determine whether or not a side effect of the contrast medium has occurred in the subject based on the temperature change of the subject.

The control unit 130 may define an interest region in the appearance image of the subject, and analyze a temperature change in the interest region. The control unit 130 may compare a predefined reference temperature with a temperature of the subject in the interest region, and determine whether or not a side effect of the contrast medium has occurred in the subject based on a result of the comparison. The predefined reference temperature may include at least one of a predefined reference absolute temperature, a predefined reference average temperature, and a predefined reference temperature variation, but exemplary embodiments are not limited thereto.

The control unit 130 may output an alarm signal when the temperature of the subject in the interest region is higher than a predefined reference temperature. The control unit 130 may output a video signal as the alarm signal via the display unit 120. Alternatively or in addition to a video signal, the control unit 130 may output an audio signal as the alarm signal via a sound output unit (not shown), or may output a vibration signal as the alarm signal via a vibration motor (not shown).

The control unit 130 may determine whether or not a side effect of the contrast medium has occurred in the subject based on the fusion image, and selectively control the medical diagnostic system 200 depending on a result of the determining whether or not a side effect of the contrast medium has occurred in the subject.

For example, the control unit 130 may control the contrast medium injection device 220 to block the injection of the contrast medium when it is determined that a side effect of the contrast medium has occurred in the subject. The control unit 130 may control the medical image acquisition device 210 to discontinue capturing a medical image of the subject when it is determined that a side effect of the contrast medium has occurred in the subject.

When a user's selection of a button for blocking the injection of the contrast medium and simultaneously discontinuing capturing of a medical image of the subject is received, the control unit 130 may transmit a control command for blocking the injection of the contrast medium to the contrast medium injection device 220, and transmit a control command for discontinuing capturing of the medical image to the medical image acquisition device 210.

The control unit 130 may request a preselected external terminal (not shown) to initiate a voice connection or may transmit a notification message to the preselected external terminal when it is determined that a side effect of the contrast medium has occurred in the subject.

According to an exemplary embodiment, the control unit 130 may determine whether or not a side effect of the contrast medium has occurred in the subject based on at least one of the appearance image and the temperature distribution image of the subject. The control unit 130 may selectively control the medical diagnostic system 200 depending on a result of the determining whether or not a side effect of the contrast medium has occurred in the subject.

Figure 22:
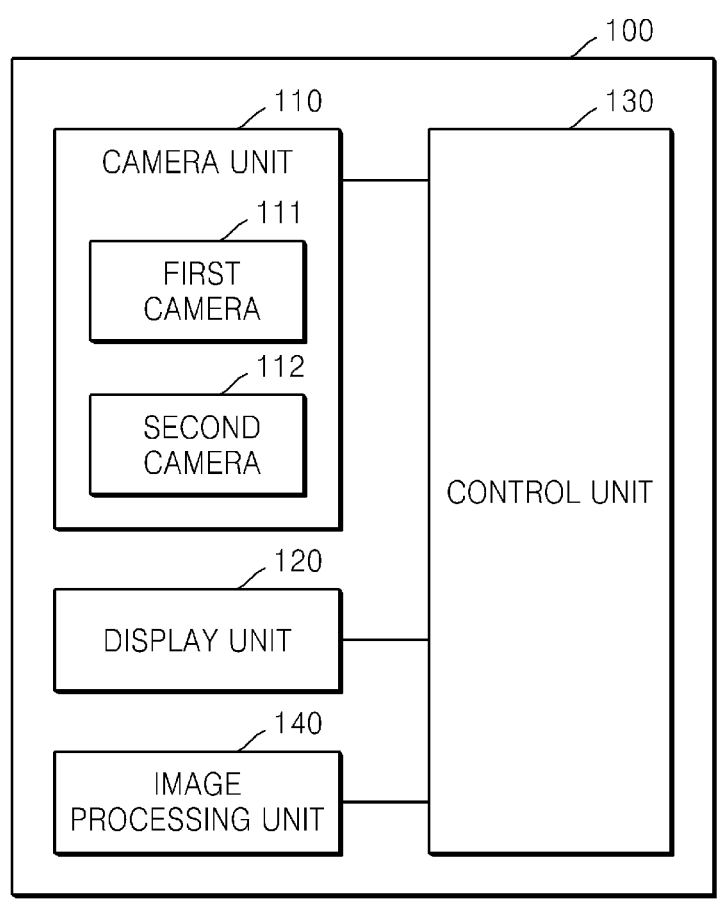
FIG. 22 is a block diagram of a medical diagnostic system control apparatus according to another exemplary embodiment.

FIG. 22 is a block diagram of a medical diagnostic system control apparatus (also referred to as a control apparatus 100) according to another exemplary embodiment.

Referring to FIG. 22, the control apparatus 100 may further include an image processing unit 140, in addition to a camera unit 110, a display unit 120, and a control unit 130. Detailed descriptions of the camera unit 110, the display unit 120, and the control unit 130, which are described above with reference to FIG. 21, will be omitted. The exemplary embodiment of FIG. 22 will be described focusing on the image processing unit 140.

The image processing unit 140 may create a fusion image of the appearance image and the temperature distribution image of the subject by using an image processing algorithm. According to an exemplary embodiment, when respective transparency levels of the appearance image and the temperature distribution image, and thereby, a fusion ratio of the fusion image of the subject, are set by a user, the image processing unit 140 may create the fusion image based on the set transparency levels or fusion ratio.

The image processing unit 140 may create a set-up window for inputting respective transparency levels or a fusion ratio of the appearance image and the temperature distribution image of the subject, a set-up window for defining an interest region in the appearance image of the subject or the fusion image, or a set-up window for inputting a reference temperature used in the determination of whether or not a side reaction of the contrast medium has occurred in the subject.

The image processing unit 140 may create a button for blocking the injection of the contrast medium, a button for discontinuing capturing of a medical image of the subject, or an integrated button for blocking the injection of the contrast medium and simultaneously discontinuing capturing of a medical image of the subject.

Figure 23:
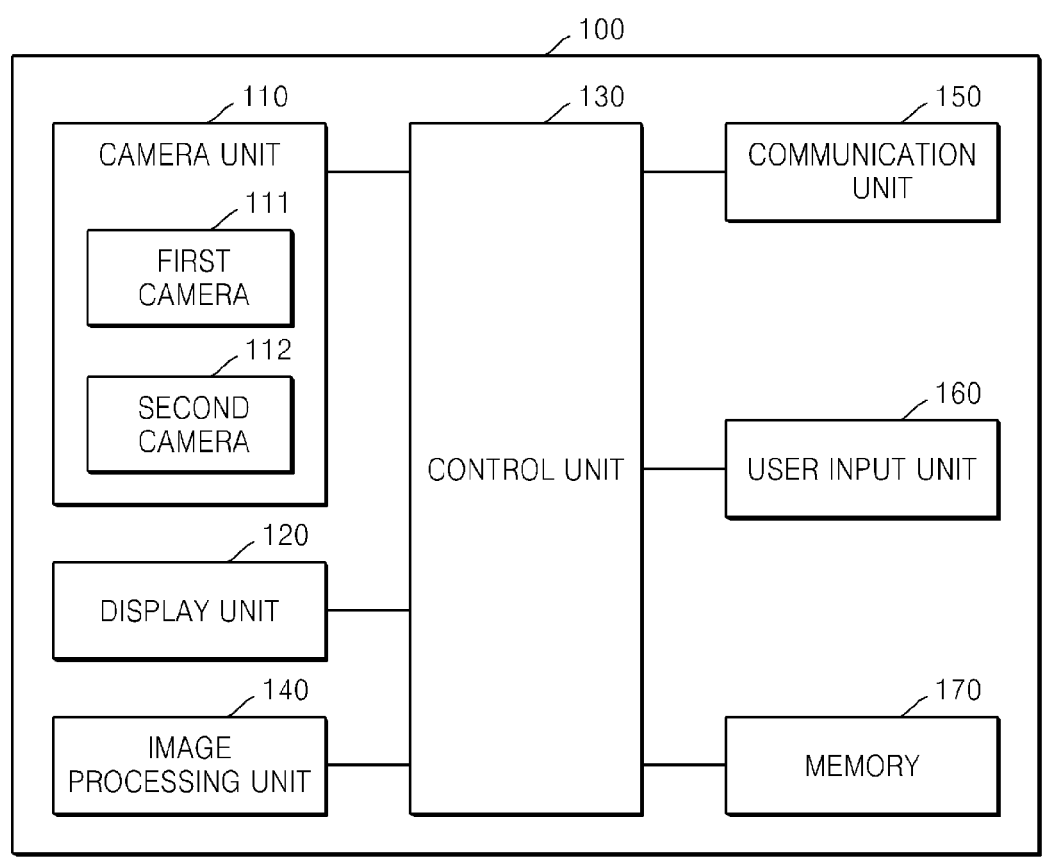
FIG. 23 is a block diagram of a medical diagnostic system control apparatus according to another exemplary embodiment.

FIG. 23 is a block diagram of a medical diagnostic system control apparatus (also referred to as a control apparatus 100) according to another exemplary embodiment.

Referring to FIG. 23, the control apparatus 100 may further include a communication unit 150, a user input unit 160, and a memory 170, in addition to a camera unit 110, a display unit 120, a control unit 130, and an image processing unit 140. Detailed descriptions of the camera unit 110, the display unit 120, the control unit 130, and the image processing unit 140, which are described above with reference to FIGS. 21 and 22, will be omitted. The exemplary embodiment of FIG. 23 will be described focusing on the communication unit 150, the user input unit 160, and the memory 170.

The communication unit 150 may include at least one element that enables communication between various devices, such as, for example, between the control apparatus 100 and the medical image acquisition device 210 (refer to FIG. 1), between the control apparatus 100 and the contrast medium injection device 220, between the control apparatus 100 and the external terminal 230, or between the control apparatus 100 and the server 240. For example, the communication unit 150 may include a short-range wireless communication module, a wired communication module, or a mobile communication module.

The short-range wireless communication module refers to a module for short-range communication within a predefined distance. Available short-range wireless communication technologies may use, but are not limited to using, radio local area network (Wi-Fi), Bluetooth, Bluetooth Low Energy (BLE), Ultra Wideband (UWB), ZigBee, Near Field Communication (NFC), Wi-Fi Direct (WFD), Infrared Data Association (IrDA), and the like.

The wired communication module refers to a module for communication using an electrical signal or an optical signal. According to exemplary embodiments, available wired communication technologies may use twisted pair cable, coaxial cable, optical fiber cable, Ethernet cable, and the like.

The wireless communication module may transmit a wireless signal to or receive the same from at least one of a base station, an external terminal, and a server on a mobile communication network. The wireless signal may include a voice call signal, a video communication call signal, or various forms of data involved in transmission and reception of text/multimedia messages).

The communication unit 150 may establish a text message session, a voice communication session, a video communication session or the like for communication with the external terminal 230. The communication unit 150 may be connected to a network in a wired or wireless manner to communicate with an external terminal (e.g., 230) (for example, a doctor's terminal or a nurse's terminal) or the server 240. The communication unit 150 may exchange data with a hospital server or another medical equipment in a hospital connected via a picture archiving and communication system (PACS). The communication unit 150 may perform data communication in accordance with the Digital Imaging and Communications in Medicine (DICOM) standard.

The user input unit 160 may be implemented as a unit via which a user (for example, a radiotherapist) may input data for controlling the control apparatus 100. For example, the user input unit 160 may be a keypad, a dome switch, a touch pad (for example, a contact-type electrostatic capacity touch pad, a pressure-type resistive touch screen, an infrared ray detection-type touch pad, a surface ultrasonic wave conduction-type touch pad, an integrated tension measurement-type touch pad, a piezoelectric effect-type touch pad, or the like), a jog wheel, or a jog switch, but exemplary embodiments are not limited thereto. For example, the user input unit 160 may further include any of a variety of input units, for example, an electrocardiogram (ECG) measurement module, a breathing measurement module, a voice recognition sensor, a gesture recognition sensor, a fingerprint recognition sensor, an iris recognition sensor, a depth sensor, a distance sensor, or a bending sensor.

According to an exemplary embodiment, the user input unit 160 may detect a real-touch and a proximity touch. The user input unit 160 may sense a touch input (for example, a touch and hold, a tap, a double-tap, or a flick) on at least one of the temperature distribution image of the subject, the appearance image of the subject, and the fusion image. The user input unit 160 may detect a drag input from a sensed touch input point. The user input unit 160 may detect multiple touch inputs (for example, a pinch input) on at least two points in a medical image.

According to an exemplary embodiment, the user input unit 160 may receive an input of the respective transparency levels via a set-up window for inputting the respective transparency levels of the appearance image and the temperature distribution image of the subject. According to another exemplary embodiment, the user input unit 160 may receive a user's input that defines one or at least two interest regions.

The memory 170 may store programs for control processes in the control unit 130 or input/output data (for example, a temperature distribution image of a subject, an appearance image of the subject, a fusion image, an interest region, a fusion ratio, a transparency level, a reference absolute temperature, a reference temperature variation, a reference average temperature, a reference temperature color, a reference facial expression change rate, and the like).

The memory 170 may include at least one storage medium, for example, a flash memory, a hard disk, a multimedia card micro, a card-type memory such as a secure digital (SD) or extreme digital (XD) memory, random access memory (RAM), static random access memory (SRAM), read-only memory (ROM), electrically erasable programmable read-only memory (EEPROM), programmable read-only memory (PROM), a magnetic memory, a magnetic disc, and an optical disc. The control apparatus 100 may operate web or cloud storage for performing a storage function of the memory 170 on a network such as the Internet.

The programs stored in the memory 170 may be classified into a plurality of modules according to functions. For example, the programs may be classified into a user interface (UI) module, a camera module, a touch screen module, and an alarm module.

The UI module may provide a specialized UI or GUI for each application. The camera module may capture and process an appearance image or a temperature distribution image of a subject. The functions of the UI module and the camera modules are intuitively deducible by one of ordinary skill in the art, and thus detailed descriptions thereof will be omitted.

The touch screen module may detect a user's touch gesture on a touch screen and transmit information about the touch gesture to the control unit 130. Various types of sensors may be disposed inside or near the touch screen, in order to detect a touch or a proximity touch on the touch screen. An example of a sensor for detecting a touch on the touch screen may be a tactile sensor. A tactile sensor is a sensor for detecting contact of a specific object to such a degree of sensitivity that humans may operate the tactile sensor. The tactile sensor may detect various types of information, such as information about a roughness of a contact surface, a hardness of a contact object, or a temperature at a contact point.

Another example of a sensor for detecting a touch on the touch screen is a proximity sensor. A proximity sensor is a sensor for detecting an object which is approaching a predetermined detection surface or a neighboring object based on the strength of an electromagnetic field or an infrared light. Examples of the proximity sensor include a transmission-type photoelectric sensor, a direct reflection-type photoelectric sensor, a mirror reflection-type photoelectric sensor, a high-frequency oscillation proximity sensor, an electrostatic capacity-type proximity sensor, a magnetic-type proximity sensor, and an infrared proximity sensor. Touch gestures of a user may be, for example, a tap, a touch and hold, a double-tap, a drag, panning, a flick, a drag-and-drop, and a swipe.

The memory 170 may include a voice recognition module (not shown) for recognizing a voice of a user by using a voice recognition engine and transmitting the recognized voice signal to the control unit 130.

The alarm module may generate a signal for notifying the generation of an event in the control apparatus 100. Examples of the event generated in the control apparatus 100 may be an event where an amount of temperature change of the subject is greater than a reference temperature change, an event where a facial expression change rate of the subject is greater than a reference facial expression change rate, or the like. The alarm module may output an alarm signal in the form of a video signal via the display unit 120, in the form of an audio signal via a sound output unit (not shown), or in the form of a vibration signal via a vibration motor (not shown), or a combination thereof.

The alarm module may provide a snooze function. For example, if a user sets the number of alarm repetitions to be, for example, 5 times, or an alarm interval to be, for example, 3 minutes, the alarm module may output an alarm signal by a predetermined number of times, for example, 5 times, or at a predetermined interval, for example, every 3 minutes.

The exemplary embodiments can be implemented in the form of executable program commands through a variety of computer devices and recordable to computer-readable media. The computer-readable media may include solely or in combination, program commands, data files, and data structures. The program commands recorded to the media may be components specially designed for the exemplary embodiments or may be usable by one of ordinary skill in the art of computer software. Types of computer-readable recording media include, for example, magnetic media such as a hard disk, a floppy disk, and a magnetic tape, optical media such as CD-ROMs and DVDs, magneto-optical media such as floptical and hardware devices such as ROM, RAM, and a flash memory specially designed to store and carry out programs. Program commands include not only machine language code generated by a compiler but also high level code that can be used by an interpreter, etc., which is executed by a computer.

As described above, according to the one or more exemplary embodiments, a medical diagnostic system control apparatus may automatically determine whether or not a side effect of the contrast medium has occurred in the subject, based on an appearance image of the subject captured via a first camera and a temperature distribution image of the subject captured via a second camera. When it is determined that the side reaction of the contrast medium has occurred in the subject, the medical diagnostic system control apparatus may rapidly respond to the occurrence of the side effect in various ways, for example, by discontinuing capturing of a medical image or blocking the injection of the contrast medium.

While the present disclosure has been particularly shown and described with reference to exemplary embodiments thereof, it will be understood by those of ordinary skill in the art that various changes in form and details may be made therein without departing from the spirit and scope of the present disclosure as defined by the following claims.

What is claimed is:

1. A method of controlling a medical diagnostic system using a contrast medium, the method comprising:
   obtaining an appearance image of a subject into whom the contrast medium has been injected, via a first camera;
   obtaining a temperature distribution image of the subject via a second camera;
   displaying a fusion image which combines the appearance image of the subject and the temperature distribution image of the subject on a screen;
   determining whether a side effect of the contrast medium has occurred in the subject, based on the fusion image; and
   selectively controlling the medical diagnostic system depending on a result of the determining.

2. The method of claim 1, wherein the first camera is a closed-circuit television (CCTV) camera, and the second camera is an infrared camera.

3. The method of claim 1, wherein the displaying of the fusion image comprises:
   displaying a set-up window configured to input respective transparency levels of the appearance image of the subject and the temperature distribution image of the subject on the screen;
   receiving an input of the respective transparency levels via the set-up window; and
   displaying the fusion image based on the input of the respective transparency levels.

4. The method of claim 1, wherein the displaying of the fusion image comprises:
   updating the fusion image in real-time; and
   displaying the updated fusion image on the screen.

5. The method of claim 1, wherein the determining of whether the side effect of the contrast medium has occurred in the subject comprises:
   measuring a facial expression change of the subject based on the appearance image of the subject; and
   determining whether the side effect of the contrast medium has occurred in the subject, based on a result of comparing the measured facial expression change of the subject and a predefined reference facial expression change.

6. The method of claim 1, wherein the determining of whether the side effect of the contrast medium has occurred in the subject comprises:
   analyzing a temperature change of the subject based on the temperature distribution image; and
   determining whether the side effect of the contrast medium has occurred in the subject, based on the analyzed temperature change of the subject.

7. The method of claim 6, wherein the analyzing of the temperature change of the subject comprises:
   defining an interest region in the appearance image of the subject; and
   analyzing a temperature change of the subject in the interest region.

8. The method of claim 7, wherein the defining of the interest region in the appearance image of the subject comprises defining a plurality of interest regions based on user input.

9. The method of claim 7, wherein the determining of whether the side effect of the contrast medium has occurred in the subject, based on the analyzed temperature change of the subject, comprises:

comparing a predefined reference temperature with a temperature of the subject in the interest region; and determining whether the side effect of the contrast medium has occurred in the subject, based on a result of the comparing.

10. The method of claim 9, wherein the comparing comprises comparing a predefined reference temperature variation with a temperature variation of the subject in the interest region.

11. The method of claim 9, wherein the comparing comprises comparing a predefined reference average temperature with an average temperature of the subject in the interest region.

12. The method of claim 9, wherein the selectively controlling of the medical diagnostic system comprises outputting an alarm signal when the temperature of the subject in the interest region is higher than the predefined reference temperature.

13. The method of claim 1, wherein the selectively controlling of the medical diagnostic system comprises controlling a contrast medium injection device for injecting the contrast medium into the subject.

14. The method of claim 13, wherein the selectively controlling of the contrast medium injection device comprises controlling the contrast medium injection device to block the injecting of the contrast medium when it is determined that the side effect of the contrast medium has occurred in the subject.

15. The method of claim 1, wherein the selectively controlling of the medical diagnostic system comprises controlling a medical image acquisition device to discontinue capturing of a medical image of the subject.

16. The method of claim 1, wherein the selectively controlling of the medical diagnostic system comprises displaying at least one of a button for blocking injection of the contrast medium and a button for discontinuing capturing of a medical image of the subject on the screen when it is determined that the side effect of the contrast medium has occurred in the subject.

17. The method of claim 1, wherein the selectively controlling of the medical diagnostic system comprises:

displaying a button for blocking the injection of the contrast medium and simultaneously discontinuing capturing of a medical image of the subject on the screen when it is determined that the side effect of the contrast medium has occurred in the subject; and transmitting a control command for blocking the injection of the contrast medium to the contrast medium injection device, and transmitting a control command for discontinuing the capturing of a medical image of the subject to a medical image acquisition device, in response to a user's selection of the button being input.

18. The method of claim 1, wherein the selectively controlling of the medical diagnostic system comprises requesting a preselected external device to initiate a voice connection or transmitting a notification message, when it is determined that the side effect of the contrast medium has occurred in the subject.

19. A method of controlling a medical diagnostic system using a contrast medium, the method comprising:

obtaining an appearance image of a subject into whom the contrast medium has been injected via a first camera;

obtaining a temperature distribution image of the subject, via a second camera;

displaying the appearance image and the temperature distribution image of the subject on a screen;

determining whether a side effect of the contrast medium has occurred in the subject, based on at least one of the appearance image of the subject and the temperature distribution image of the subject; and selectively controlling the medical diagnostic system depending on a result of the determining.

20. A method of providing an image of a subject into whom a contrast medium has been injected, the method comprising:

obtaining an appearance image of the subject via a first camera;

obtaining a temperature distribution image of the subject via a second camera;

creating a fusion image which combines the appearance image and the temperature distribution image of the subject;

displaying the fusion image on a screen; and determining whether a side effect of the contrast medium has occurred in the subject based on the fusion image.

21. The method of claim 20, wherein the creating of the fusion image comprises:

displaying a set-up window configured to input respective transparency levels of the appearance image of the subject and the temperature distribution image of the subject on the screen;

receiving an input of the respective transparency levels via the set-up window; and creating the fusion image of the appearance image and the temperature distribution image of the subject based on the input of the respective transparency levels.

22. The method of claim 20, further comprising selectively controlling a medical diagnostic system depending on a result of the determining.

23. A method of controlling a medical diagnostic system using a contrast medium, the method comprising:

displaying a temperature distribution image of a subject into whom the contrast medium has been injected;

determining whether a side effect of the contrast medium has occurred in the subject, based on the temperature distribution image; and selectively controlling the medical diagnostic system depending on a result of the determining.

24. A method of controlling a medical diagnostic system using a contrast medium, the method comprising:

displaying an appearance image of a subject into whom the contrast medium has been injected;

measuring a facial expression change of the subject based on the appearance image of the subject;

determining whether a side effect of the contrast medium has occurred in the subject, based on a result of comparing the measured facial expression change of the subject and a predefined reference facial expression change; and selectively controlling the medical diagnostic system depending on a result of the determining.

25. An apparatus configured to control a medical diagnostic system, the apparatus comprising:

a first camera configured to obtain an appearance image of a subject into whom a contrast medium has been injected;

a second camera configured to obtain a temperature distribution image of the subject;

a display configured to display a fusion image which combines the appearance image of the subject and the temperature distribution image of the subject on a screen; and a controller unit configured to make a determination as to whether a side effect of the contrast medium has occurred in the subject, based on the fusion image, and to selectively control the medical diagnostic system depending on a result of the determination.

26. The apparatus of claim 25, wherein the first camera is a closed-circuit television (CCTV) camera, and the second camera is an infrared camera.

27. The apparatus of claim 25, wherein the medical diagnostic system comprises at least one of a medical image acquisition device configured to obtain a medical image of the subject and a contrast medium injection device configured to automatically inject the contrast medium into the subject.

28. The apparatus of claim 27, wherein the medical image acquisition device comprises at least one of a computed tomography (CT) image scanning apparatus, an angiography apparatus, and a magnetic resonance imaging (MRI) apparatus.

29. The apparatus of claim 25, wherein the display is configured to display a set-up window for inputting respective transparency levels of the appearance image of the subject and the temperature distribution image of the subject.

30. The apparatus of claim 29, further comprising a user inputter configured to receive an input of the respective transparency levels via the set-up window, wherein the display is configured to display the fusion image based on the input of the respective transparency levels.

31. The apparatus of claim 25, wherein the control is configured to measure a facial expression change of the subject based on the appearance image of the subject, and determine whether the side effect of the contrast medium has occurred in the subject, based on a result of comparing the measured facial expression change of the subject and a predefined reference facial expression change.

32. The apparatus of claim 25, wherein the control is configured to analyze a temperature change of the subject based on the temperature distribution image and determine whether the side effect of the contrast medium has occurred in the subject, based on the analyzed temperature change of the subject.

33. The apparatus of claim 32, wherein the control is configured to define an interest region in the appearance image of the subject and analyze a temperature change of the subject in the interest region.

34. The apparatus of claim 33, further comprising a user inputter configured to receive a user input defining a plurality of interest regions.

35. The apparatus of claim 33, wherein the controller is configured to compare a predefined reference temperature and a temperature of the subject in the interest region, and determine whether the side effect of the contrast medium has occurred in the subject, based on a result of the comparison.

36. The apparatus of claim 35, wherein the predefined reference temperature comprises at least one of a predefined reference absolute temperature, a predefined reference average temperature and a predefined reference temperature variation.

37. The apparatus of claim 35, wherein the controller is configured to output an alarm signal when the temperature of the subject in the interest region is higher than the predefined reference temperature.

38. The apparatus of claim 25, wherein the controller is configured to control a contrast medium injection device to block the injection of the contrast medium when it is determined that the side effect of the contrast medium has occurred in the subject.

39. The apparatus of claim 25, wherein the controller is configured to control a medical image acquisition device to discontinue capturing of a medical image of the subject when it is determined that the side effect of the contrast medium has occurred in the subject.

40. The apparatus of claim 25, wherein the display is configured to display at least one of a button which blocks injection of the contrast medium and a button which discontinues capturing of a medical image of the subject when it is determined that the side effect of the contrast medium has occurred in the subject.

41. The apparatus of claim 25, wherein the display is configured to display a button which blocks injection of the contrast medium and simultaneously discontinues capturing of a medical image of the subject when it is determined that the side effect of the contrast medium has occurred in the subject, and
the controller is configured to transmit a control command which blocks injection of the contrast medium to a contrast medium injection device, and transmit a control command which discontinues capturing of a medical image of the subject to a medical image acquisition device, when a user's selection of the button is received.

42. The apparatus of claim 25, wherein the controller is configured to request a preselected external device to initiate a voice connection or transmit a notification message, when it is determined that the side effect of the contrast medium has occurred in the subject.

43. An apparatus configured to control a medical diagnostic system, the apparatus comprising:
a first camera configured to obtain an appearance image of a subject into whom a contrast medium is injected;
a second camera configured to obtain a temperature distribution image of the subject;
a display configured to display the appearance image of the subject and the temperature distribution image of the subject; and
a controller configured to make a determination as to whether a side effect of the contrast medium has occurred in the subject, based on at least one of the appearance image of the subject and the temperature distribution image of the subject, and to selectively control the medical diagnostic system depending a result of the determination.

44. An apparatus configured to control a medical diagnostic system, the apparatus comprising:
a first camera configured to obtain an appearance image of a subject into whom a contrast medium has been injected;
a second camera configured to obtain a temperature distribution image of the subject;
an image processor configured to create a fusion image which combines the appearance image of the subject and the temperature distribution image of the subject;
a display configured to display the fusion image; and
a controller configured to make a determination as to whether a side effect of the contrast medium has occurred in the subject based on the fusion image and to control the first camera, the second camera, the image processor, and the display based on the determination.

45. A non-transitory computer-readable recording medium having recorded thereon a program which, when executed by a computer, causes the computer to perform a medical diagnostic system control method comprising:
obtaining an appearance image of a subject into whom a contrast medium has been injected, via a first camera;
obtaining a temperature distribution image of the subject via a second camera;
displaying a fusion image which combines the appearance image of the subject and the temperature distribution image of the subject on a screen;

determining whether a side effect of the contrast medium has occurred in the subject, based on the fusion image; and selectively controlling a medical diagnostic system depending on a result of the determining.

* * * * *